United States Patent
Deng et al.

(10) Patent No.: US 12,099,048 B2
(45) Date of Patent: Sep. 24, 2024

(54) AQUATIC ORGANISM MONITORING DEVICES AND AQUATIC ORGANISM MONITORING METHODS

(71) Applicant: Battelle Memorial Institute, Richland, WA (US)

(72) Inventors: Z. Daniel Deng, Richland, WA (US); Yang Yang, Richland, WA (US); Jun Lu, Richland, WA (US); Huidong Li, Richland, WA (US); Jayson J. Martinez, Kennewick, WA (US); Brett D. Pflugrath, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 486 days.

(21) Appl. No.: 16/951,251

(22) Filed: Nov. 18, 2020

(65) Prior Publication Data

US 2021/0148881 A1    May 20, 2021

Related U.S. Application Data

(60) Provisional application No. 62/937,613, filed on Nov. 19, 2019.

(51) Int. Cl.
*G01N 33/18* (2006.01)
*A01K 11/00* (2006.01)
*A01K 61/90* (2017.01)

(52) U.S. Cl.
CPC ....... *G01N 33/186* (2013.01); *G01N 33/1886* (2013.01); *A01K 11/006* (2013.01); *A01K 61/90* (2017.01); *Y02A 40/81* (2018.01)

(58) Field of Classification Search
CPC .... A01K 61/90; A01K 11/006; G01N 33/186; G01N 33/1886; Y02A 40/81
See application file for complete search history.

(56) References Cited

U.S. PATENT DOCUMENTS

| 5,502,656 A | 3/1996 | Fulcher et al. |
| 6,662,742 B2 | 12/2003 | Shelton et al. |

(Continued)

FOREIGN PATENT DOCUMENTS

| AU | 2020102206 A4 * | 10/2020 |
| CN | 102768268 | 11/2012 |

(Continued)

OTHER PUBLICATIONS

Machine Translation of CN 108617533A (Year: 2018).*

(Continued)

*Primary Examiner* — Nathaniel J Kolb
(74) *Attorney, Agent, or Firm* — Wells St. John P.S.

(57) ABSTRACT

Aquatic organism monitoring devices and aquatic organism monitoring methods are described. According to one aspect, a monitoring device includes a housing configured to be physically associated with an aquatic organism, environmental circuitry configured to generate a first output indicative of at least one environmental parameter of an environment of the organism, behavioral circuitry coupled with the housing and configured to generate a second output indicative of at least one behavioral parameter of the organism, physiological circuitry coupled with the housing and configured to generate a third output indicative of at least one physiological parameter of the organism, and a transmitter configured to transmit an acoustic signal externally of the housing, and wherein the acoustic signal includes information regarding one or more of the at least one environmental parameter, the at least one behavioral parameter, and the at least one physiological parameter.

34 Claims, 15 Drawing Sheets

(56) References Cited

U.S. PATENT DOCUMENTS

| | | | |
|---|---|---|---|
| 7,662,386 | B2 | 1/2010 | Donelan et al. |
| 8,636,648 | B2 | 1/2014 | Gazdzinski |
| 9,629,340 | B2 | 4/2017 | Schab et al. |
| 9,894,885 | B2 | 2/2018 | Schab et al. |
| 10,033,469 | B2 | 7/2018 | Deng et al. |
| 10,033,470 | B2 | 7/2018 | Deng et al. |
| 10,067,112 | B2 | 9/2018 | Deng et al. |
| 10,101,429 | B2 | 10/2018 | Deng et al. |
| 10,154,655 | B2 | 12/2018 | Schab et al. |
| 10,236,920 | B2 | 3/2019 | Deng et al. |
| 10,433,036 | B1* | 10/2019 | Shafer ............... H04Q 9/02 |
| 10,531,639 | B2 | 1/2020 | Deng et al. |
| 10,645,905 | B2 | 5/2020 | Gandola et al. |
| 10,739,434 | B2 | 8/2020 | Deng et al. |
| 10,935,536 | B2 | 3/2021 | Deng et al. |
| 11,139,840 | B2 | 10/2021 | Deng et al. |
| 11,278,004 | B2 | 3/2022 | Deng et al. |
| 11,355,005 | B2 | 6/2022 | Deng et al. |
| 11,381,263 | B2 | 7/2022 | Deng et al. |
| 11,533,818 | B2 | 12/2022 | Deng et al. |
| 2008/0080318 | A1 | 4/2008 | Maxwell et al. |
| 2012/0134239 | A1 | 5/2012 | Struthers |
| 2015/0063072 | A1* | 3/2015 | Deng ............... H01M 10/0569 367/134 |
| 2015/0237834 | A1 | 8/2015 | Schab et al. |
| 2015/0250140 | A1 | 9/2015 | Fraser et al. |
| 2015/0289479 | A1* | 10/2015 | Allen ............... A01K 11/006 367/137 |
| 2016/0037749 | A1 | 2/2016 | Gandola et al. |
| 2016/0211924 | A1 | 7/2016 | Deng et al. |
| 2016/0245894 | A1 | 8/2016 | Deng et al. |
| 2017/0089878 | A1* | 3/2017 | Deng ............... G01N 33/1886 |
| 2017/0107138 | A1 | 4/2017 | McLaine |
| 2017/0127975 | A1* | 5/2017 | Bozkurt ............... A01K 29/005 |
| 2017/0223931 | A1 | 8/2017 | Schab et al. |
| 2018/0055007 | A1* | 3/2018 | Deng ............... H04B 11/00 |
| 2018/0263220 | A1 | 9/2018 | Schab et al. |
| 2019/0059338 | A1 | 2/2019 | Schab et al. |
| 2020/0137980 | A1* | 5/2020 | Deng ............... H04B 11/00 |
| 2020/0137982 | A1 | 5/2020 | Hussain et al. |
| 2020/0358067 | A1 | 11/2020 | Deng et al. |
| 2020/0404882 | A1 | 12/2020 | Gandola et al. |
| 2021/0190753 | A1 | 6/2021 | Deng et al. |
| 2022/0079116 | A1 | 3/2022 | Deng et al. |
| 2022/0272942 | A1 | 9/2022 | Deng et al. |
| 2022/0361460 | A1 | 11/2022 | Deng et al. |
| 2023/0131728 | A1 | 4/2023 | Deng et al. |

FOREIGN PATENT DOCUMENTS

| | | | | |
|---|---|---|---|---|
| CN | 108617533 | A * | 10/2018 | ........... A01K 11/006 |
| NO | 20190557 | A1 * | 4/2019 | |
| WO | WO 2010/105846 | | 9/2010 | |
| WO | WO-2014151852 | A1 * | 9/2014 | ........... A01K 11/003 |
| WO | WO-2019160645 | A1 * | 8/2019 | ........... A01K 11/004 |
| WO | WO PCT/US2020/060991 | | 5/2022 | |

OTHER PUBLICATIONS

Block et al., "Electronic Tagging and Population Structure of Atlantic Bluefin Tuna", Nature vol. 434, Apr. 2005, United Kingdom, pp. 1121-1127.

Block et al., "Tracking Apex Marine Predator Movements in a Dynamic Ocean", Nature vol. 475, 2011, United Kingdom, 5 pages.

Broell et al., "Measuring Abnormal Movements in Free-Swimming Fish with Accelerometers: Implications for Quantifying Tag and Parasite Load", Journal of Experimental Biology vol. 219, 2016, United Kingdom, pp. 695-705.

Brown et al., "An Evaluation of the Maximum Tag Burden for Implantation of Acoustic Transmitters in Juvenile Chinook Salmon", North American Journal of Fisheries Management vol. 30, 2010, United States, pp. 499-505.

Chen et al., "Micro-Battery Development for Juvenile Salmon Acoustic Telemetry System Applications", Scientific Reports 3790, 2014, United Kingdom, 5 pages.

Cooke et al., "Activity and Energetics of Free-Swimming Fish: Insights from Electromyogram Telemetry". Fish and Fisheries vol. 5, 2004, United Kingdom, pp. 21-52.

De Almeida et al., "Testing a 3-Axis Accelerometer Acoustic Transmitter (AccelTag) on the Lusitanian Toadfish", Journal of Experimental Marine Biology and Ecology vol. 449, 2013, Netherlands, pp. 230-238.

Deng et al., "An Injectable Acoustic Transmitter for Juvenile Salmon", Scientific Reports 5(1), 2015, United Kingdom, 6 pages.

Deng et al., U.S. Appl. No. 62/937,613, filed Nov. 19, 2019, titled "LAB-ON-A-FISH", 82 pages.

Dewar et al., "Development of an Acoustic Telemetry Tag for Monitoring Electromyograms in Free-Swimming Fish", Journal of Experimental Biology vol. 202, 1999, United Kingdom, pp. 2693-2699.

Donaldson et al., "Making Connections in Aquatic Ecosystems with Acoustic Telemetry Monitoring". Frontiers in Ecology and the Environment vol. 12(10), 2014, United States, pp. 565-573.

Gleiss et al., "Accelerating Estimates of Activity-Specific Metabolic Rate in Fishes: Testing the Applicability of Acceleration Data-Loggers", Journal of Experimental Marine Biology and Ecology vol. 385, Issues 1-2, Apr. 2010, Netherlands, pp. 85-91.

Graesli et al., "Seasonal Hypometabolism in Female Moose", Frontiers in Ecology and Evolution vol. 8, Article 107, May 2020, Switzerland, 12 pages.

Harcourt et al., "Animal-Borne Telemetry: An Integral Component of the Ocean Observing Toolkit", Frontiers in Marine Science vol. 6, Article 326, 2019, Switzerland, 21 pages.

Harrison et al., "The Political Biogeography of Migratory Marine Predators", Nature Ecology and Evolution 2(10), 2018, United States, 11 pages.

Hussey et al., "Aquatic Animal Telemetry: A Panoramic Window into the Underwater World", Science vol. 348, Issue 6240, Jun. 2015, United States, 12 pages.

Irvine et al., "Sperm Whale Dive Behavior Characteristics Derived from Intermediate-Duration Archival Tag Data", Ecology and Evolution, 2017, United Kingdom, 16 pages.

Kaseloo et al., "A Biotelemetry System for Recording Fish Activity", Journal of Fish Biology vol. 40, Issue 2, Feb. 1992, United Kingdom, pp. 165-179.

Kawabata et al., "Use of a Gyroscope/Accelerometer Data Logger to Identify Alternative Feeding Behaviors in Fish", The Journal of Experimental Biology vol. 217, 2014, United Kingdom, pp. 3204-3208.

Kays et al., "Terrestrial Animal Tracking as an Eye on Life and Plant", Science vol. 348, Issue 6240, 2015, United States, 10 pages.

Keefe et al., "Positioning Methods and the Use of Location and Activity Data in Forests", Forests 10(5):458, 2019, United States, 46 pages.

Kessel et al., "Predictable Temperature-Regulated Residency, Movement and Migration in a Large, Highly Mobile Marine Predator (Negaprion Brevirostris)", Marine Ecology Progress Series vol. 514, 2014, Germany, pp. 175-190.

Khan et al., "A Flexible Organic Reflectance Oximeter Array", Proceedings of the National Academy of Sciences of the United States of America (PNAS) vol. 115, No. 47, 2018, United States, 10 pages.

Kilfoyle et al., "The State of the Art in Underwater Acoustic Telemetry", IEEE Journal of Oceanic Engineering vol. 25, No. 1, Jan. 2000, United States, pp. 4-27.

Laplanche et al., "Tracking Marine Mammals in 3D Using Electronic Tag Data", Methods in Ecology and Evolution, 2015, United States, 10 pages.

Larocque et al., "Survival and Migration Patterns of Naturally and Hatchery-Reared Atlantic Salmon (Salmo Salar) Smolts in a Lake Ontario Tributary using Acoustic Telemetry", Freshwater Biology vol. 65, 2020, United Kingdom, pp. 835-848.

Li et al., "Design Parameters of a Miniaturized Piezoelectric Underwater Acoustic Transmitter", Sensors vol. 12, 2012, Switzerland, pp. 9098-9109.

(56) References Cited

OTHER PUBLICATIONS

Lochner et al., "All-Organic Optoelectronic Sensor for Pulse Oximetry", Nature Communications vol. 5, 2014, United Kingdom, 7 pages.
Lowerre-Barbieri et al., "The Ocean's Movescape: Fisheries Management in the Bio-Logging Decade (2018-2028)", ICES Journal of Marine Science vol. 76, 2019, United Kingdom, 12 pages.
Lu et al., "A Small Long-Life Acoustic Transmitter for Studying the Behavior of Aquatic Animals", Review of Scientific Instruments vol. 87, 2016, United States, 6 pages.
Madigan et al., "Assessing Niche Width of Endothermic Fish from Genes to Ecosystem", Proceedings of the National Academy of Sciences (PNAS) vol. 112, No. 27, Jul. 2015, United States, pp. 8350-8355.
March et al., "Towards the Integration of Animal-Borne Instruments into Global Ocean Observing Systems", Global Change Biology vol. 26, 2020, United Kingdom, pp. 586-596.
Metcalfe et al., "Recent Advances in Telemetry for Estimating the Energy Metabolism of Wild Fishes", Journal of Fish Biology vol. 88, 2016, United Kingdom, pp. 284-297.
Metcalfe et al., "Tracking Fish with Electronic Tags", Nature vol. 387, Jun. 1997, United Kingdom, pp. 665-666.
Mitsunaga et al., "Heart Rate Telemetry of Red Sea Bream Using an Ultrasonic Transmitter", Fisheries Engineering vol. 40, No. 1, 2003, Japan, pp. 23-28.
Mueller et al., "Implantation of a New Micro Acoustic Tag in Juvenile Pacific Lamprey and American Eel", Journal of Visualized Experiments vol. 145, Mar. 2019, United States, 8 pages.
Noda et al., "Animal-Mounted Gyroscope/Accelerometer/ Magnetometer: In Situ Measurement of the Movement Performance of Fast-Start Behaviour in Fish", Journal of Experimental Marine Biology and Ecology vol. 451, Feb. 2014, Netherlands, pp. 55-68.
Noda et al., "Monitoring Escape and Feeding Behaviours of Cruiser Fish by Inertial and Magnetic Sensors", PLOS ONE vol. 8, Issue 11, Nov. 2013, United States, 13 pages.
Pan et al., "A Real-Time QRS Detection Algorithm", IEEE Transactions on Biomedical Engineering vol. BME-32, No. 3, Mar. 1985, United States, pp. 230-236.
Queiroz et al., "Global Spatial Risk Assessment of Sharks Under the Footprint of Fisheries", Nature vol. 572, Aug. 2019, United Kingdom, pp. 461-466.
Song et al., "Editorial Underwater Acoustic Communications: Where We Stand and What is Next?", IEEE Journal of Oceanic Engineering vol. 44, No. 1, Jan. 2019, United States, pp. 1-6.
Steffensen et al., "Conditional Capture Probability of Pallid Sturgeon in Benthic Trawls", North American Journal of Fisheries Management vol. 35, 2015, United States, pp. 626-631.
Stehfest et al., "The Use of Acoustic Accelerometer Tags to Determine Seasonal Changes in Activity and Catchability of a Recreationally Caught Marine Teleost", ICES Journal of Marine Science vol. 72, No. 8, 2015, United Kingdom, pp. 2512-2520.
Wang et al., "Fundamental Understanding and Rational Design of High Energy Structural Microbatteries", Nano Energy vol. 43, Jan. 2018, Netherlands, pp. 310-316.
Wang et al., "Lithium and Lithium Ion Batteries for Applications in Microelectronic Devices: A Review", Journal of Power Sources 286, 2015, Netherlands, pp. 330-345.
Whitlock et al., "Direct Quantification of Energy Intake in an Apex Marine Predator Suggests Physiology is a Key Driver of Migrations", Science Advances, 2015, United States, 10 pages.
Wilga et al., "Locomotion in Sturgeon: Function of the Pectoral Fins", Journal of Experimental Biology vol. 202, 1999, United Kingdom, pp. 2413-2432.
Wilmers et al., "The Golden Age of Bio-Logging: How Animal-Borne Sensors are Advancing the Frontiers of Ecology", Ecology vol. 96 (7), 2015, United States, pp. 1741-1753.
Wu et al., "Good Practices for Rechargeable Lithium Metal Batteries", Journal of The Electrochemical Society vol. 166 (16), 2019, United States, pp. A4141-A4149.
Xiao et al., "Understanding and Applying Coulombic Efficiency in Lithium Metal Batteries", Nature Energy vol. 5, Aug. 2020, United States, pp. 561-568.
Yang et al., "Multifunctional and Miniaturized Flexible Sensor Patch: Design and Application for In Situ Monitoring of Epoxy Polymerization", Sensors and Actuators B: Chemical vol. 261, 2018, Netherlands, pp. 144-152.
Yang, "Multi-Tier Computing Networks for Intelligent IoT", Nature Electronics vol. 2, Jan. 2019, United Kingdom, pp. 4-5.

\* cited by examiner

AQUATIC ORGANISM MONITORING DEVICES AND AQUATIC ORGANISM MONITORING METHODS

RELATED PATENT DATA

This application claims the benefit of U.S. Provisional Patent Application Ser. No. 62/937,613, filed Nov. 19, 2019, titled "Lab-on-a-Fish", the disclosure of which is incorporated herein by reference.

STATEMENT AS TO RIGHTS TO INVENTIONS MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

TECHNICAL FIELD

This disclosure relates to aquatic organism monitoring devices and aquatic organism monitoring methods.

BACKGROUND OF THE DISCLOSURE

Aquatic biotelemetry technologies have been developed to monitor and study organisms in marine, freshwater, and estuarine ecosystems. Systems have been developed to monitor larger species, e.g., the blue whale (*Balaenoptera musculus*), Atlantic bluefin tuna (*Thunnus thynnus*), and lemon shark (*Negaprion brevirostris*) to significantly smaller ones such as the American eel (*Anguilla rostrata*), juvenile Pacific salmon (*Oncorhynchus* spp.), and juvenile white sturgeon (*Acipenser transmontanus*). These systems aid in future global aquatic environment management and conservation strategies.

Animal-borne biotelemetric devices (referred to as tags) are used to monitor aquatic species. The tags may be attached to a specimen to be studied and the tags thereafter transmit signals as the specimen or host moves throughout its environment. A receiver receives the signals that have been emitted by the tags and the signals may be studied to obtain information regarding the tagged host. For example, data from the tags may be used to estimate survival of fish through dams and other routes of passage.

At least some aspects of the disclosure are directed to systems and methods for monitoring aquatic organisms in aquatic environments and ecosystems.

BRIEF DESCRIPTION OF THE DRAWINGS

Example embodiments of the disclosure are described below with reference to the following accompanying drawings.

DETAILED DESCRIPTION OF THE DISCLOSURE

This disclosure is submitted in furtherance of the constitutional purposes of the U.S. Patent Laws "to promote the progress of science and useful arts" (Article 1, Section 8).

Some of the example embodiments disclosed herein are directed towards aquatic organism monitoring systems including monitoring devices that are physically associated with respective organisms (e.g., via surgical implantation of the monitoring devices within the aquatic organisms) to be tracked and monitored, and associated monitoring methods.

The monitoring devices are configured to monitor a plurality of different parameters including physiological and behavior parameters of the organisms as well as environmental parameters of the environment of the aquatic organisms in illustrative embodiments of the disclosure discussed below. Some embodiments of the disclosure provide wireless in vivo monitoring of aquatic organisms' physiology, behavior, and ambient environment. More specific example embodiments described herein are directed to monitoring devices that generate in vivo electrocardiogram (ECG) and electromyogram (EMG) waveforms and in vivo motion (triaxial gyration and triaxial acceleration) signals for monitoring of physiological and behavioral parameters of example aquatic species including rainbow trout (*Oncorhynchus mykiss*), white sturgeon (*Acipenser transmontanus*), and walleye (*Sander vitreus*). In addition, environmental parameters such as temperature, pressure and/or magnetic field of the environment of the species are also monitored in some embodiments.

Figure 1:
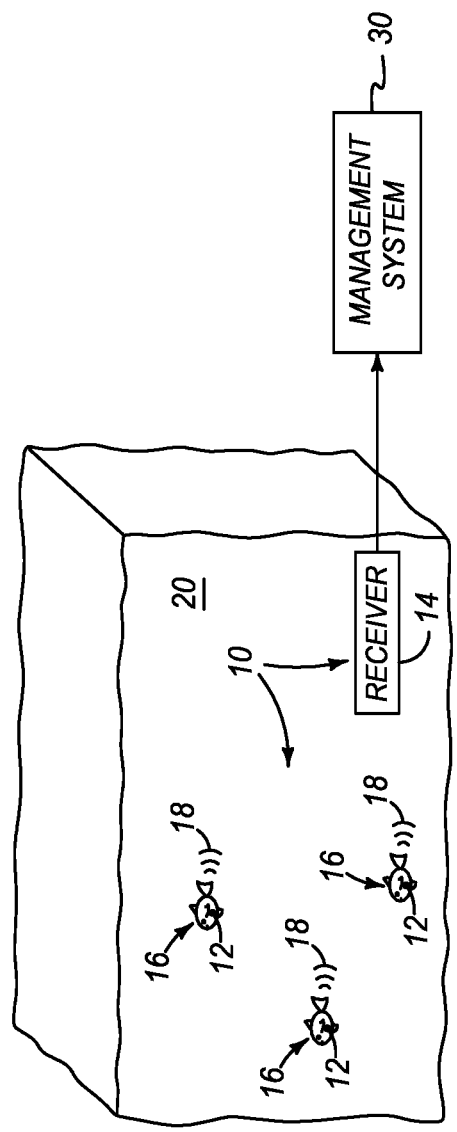
FIG. 1 is an illustrative representation of an aquatic organism monitoring system according to one embodiment.

Referring to FIG. 1, one example embodiment of an aquatic organism monitoring system 10 is shown. The illustrated system 10 includes a plurality of aquatic organism monitoring devices 12 that are associated with a plurality of aquatic organisms 16, such as fish, to be monitored and the organisms having associated devices 12 may be referred to as tagged organisms. For example, a monitoring device 12 may be received and embedded within the body of an individual aquatic organism 16 by surgery.

The depicted system 10 further includes a receiver 14 within a body of water 20 and a management system 30. Monitoring devices 12 emit a plurality of data transmissions 18 at a plurality of moments in time (e.g., periodic) that propagate through surrounding water and are received by receiver 14. Although not shown, the system 10 typically includes a plurality of receivers 14 that are positioned at different locations within the body of water 20 to receive the data transmissions 18 as the organisms 16 move throughout the body of water 20. The data transmissions 18 enable tracking or monitoring of the organisms as the organisms move throughout their natural aquatic environment.

The monitoring devices 12 may include a respective unique identification (ID) code within its transmissions 18 to enable unique tracking of individual organisms 16. In addition, information regarding one or more physiological, behavioral and/or environmental sensors of the monitoring devices 12 may also be included within the data transmissions 18 as discussed in detail below. The information may be raw data outputted by sensors of the device and/or information resulting from processing of the raw data by on-board processing circuitry in example embodiments.

In some embodiments, the receiver 14 transmits the unique ID codes and data within the received transmissions 18 to a management system 30 described below with respect to one example embodiment in FIG. 2. The locations of the individual tagged organisms 16 may be generally monitored using the identification codes and the locations of the receivers 14 that received the data transmissions 18 including the identification codes. In addition, times of arrival of data transmissions 18 at a plurality of receivers 14 may be used to triangulate the locations of the organisms 16 with increased accuracy.

Figure 2:
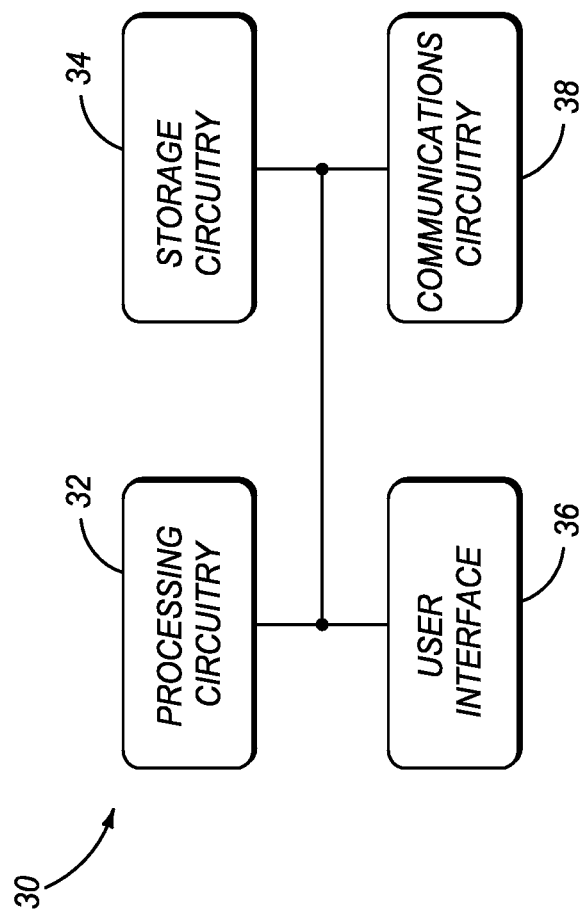
FIG. 2 is a functional block diagram of a management system according to one embodiment.

Referring to FIG. 2, one embodiment of a management system 30 of the aquatic organism monitoring system 10 is shown. Management system 30 is configured to receive information included in the data transmissions from devices 12 that are associated with respective aquatic organisms 16 from one or more receivers 14. In illustrative examples, information of the data transmissions 18 that are emitted from the monitoring devices 12 and received by receiver 14 is communicated to the management system 30 to permit study of one or more of the environmental, behavioral and physiological parameters being monitored with respect to the tagged organisms 16 and storage of the data for later use.

In the illustrated example embodiment, management system 30 includes processing circuitry 32, storage circuitry 34, a user interface 36, and communications circuitry 38. Other embodiments of management system 30 are possible including more, less and/or alternative components.

In one embodiment, processing circuitry 32 is arranged to process received data, control data access and storage, control and process interactions with a user, issue commands, and control other desired operations of system 10. Processing circuitry 32 may comprise circuitry (e.g., microprocessor) configured to implement desired programming such as ordered instructions of a program stored upon appropriate computer-readable storage media in at least one embodiment.

Storage circuitry 34 is configured to store programming such as executable code or instructions (e.g., software and/or firmware), data received from monitoring devices 12, databases, and other digital information and may include computer-readable storage media, such as memory, a disk drive, etc.

User interface 36 is configured to interact with a user including conveying data to a user (e.g., displaying visual images regarding results of the monitoring of organisms 16 for observation by the user) as well as receiving inputs from the user. For example, the information regarding the environmental, behavioral and physiological parameters may be correlated with respect to each other, for example, with respect to time and graphed for observation by a user. User interface 36 is configured as graphical user interface (GUI) in one embodiment and may be configured differently in other embodiments.

Communications circuitry 38 is configured to receive communications from receivers 14 that include information or data within transmissions 18 from the monitoring devices 12 and received by receivers 14. The information is provided to processing circuitry 32 for further processing of the data and monitoring the organisms 16. Communications circuitry 38 may implement wired or wireless communications with the receivers 14 in example embodiments.

The unique codes of transmissions 18 from the monitoring devices 12 received by the receivers 14, the locations of the receivers 14 and timestamps indicating the moments in time when the transmissions 18 were received by the receivers 14 may be stored in a database of storage circuitry 34 for subsequent usage.

Figure 3:
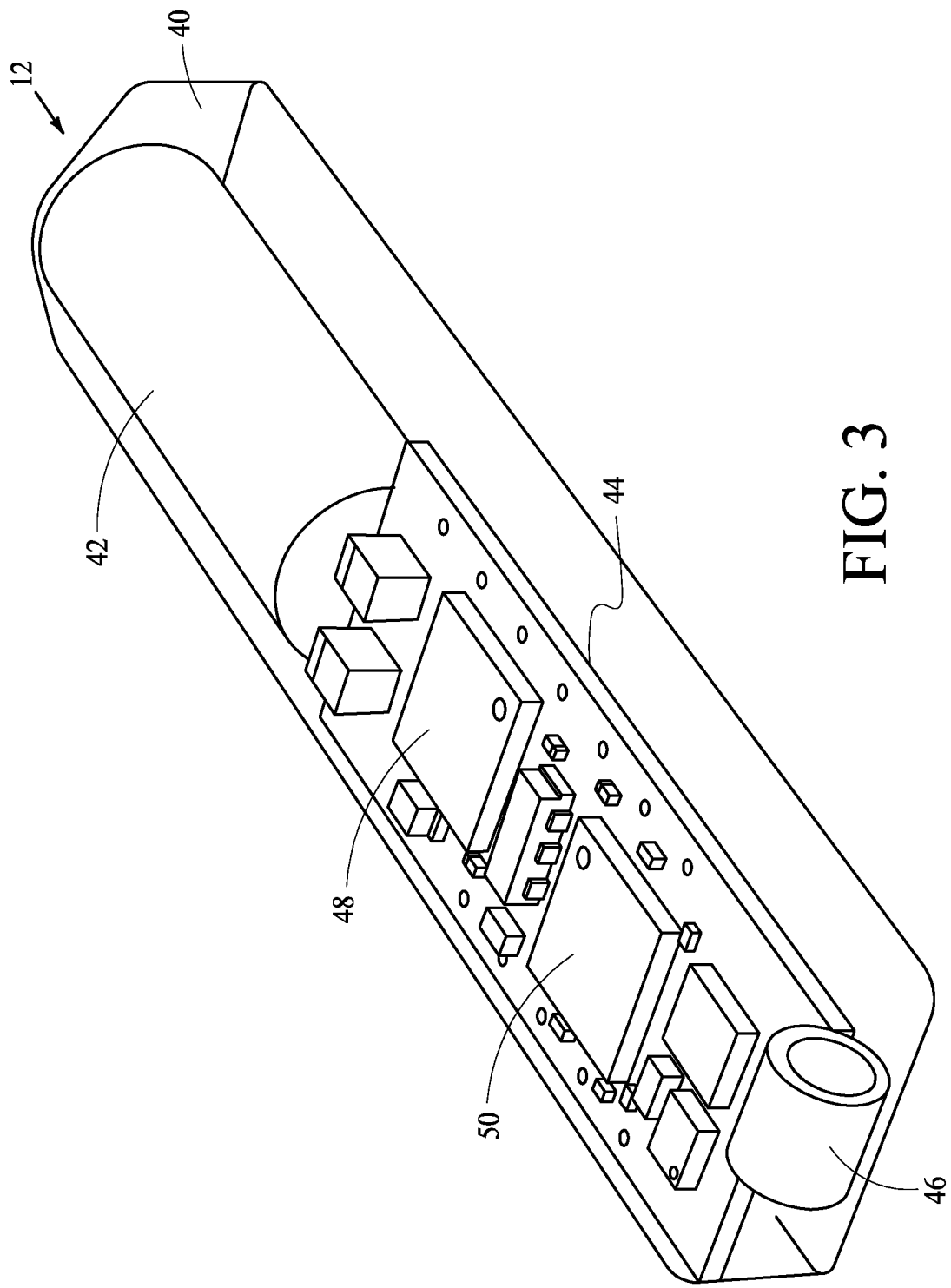
FIG. 3 is an isometric view of a monitoring device according to one embodiment.

Referring to FIG. 3, one embodiment of a monitoring device 12 is shown. The illustrated monitoring device 12 includes a housing 40, a microbattery 42, a printed circuit board 44, an acoustic transmitter or transducer 46, storage circuitry in the form of a flash integrated circuit 48 and processing circuitry in the form of a microcontroller 50. The monitoring devices 12 discussed herein may be fabricated using small footprint, high-performance, low-power operation, and commercially available electronic components in some embodiments.

The components of the monitoring device 12 are encapsulated in a suitable biocompatible epoxy that forms housing 40. One example epoxy that may be used is Scotchcast Electrical Resin 5 available from 3M Company. The epoxy may be degassed to be free of air bubbles and cured for 24 hours at room temperature. A file may be used to remove sharp edges on the device 12 to create a chamfer so the device does not cause abrasion to the organism's internal organs after being received with the body of the aquatic organism, such as by surgical implantation.

In one embodiment, microcontroller 50 is a high-performance and low-power microcontroller module (MCU) PIC24FJ64GA702 available from Microchip Technology Inc., USA with a broad peripheral feature set.

This example MCU 50 contains timing modules, a range of serial communication peripherals, including I2C, UART, SPI modules, to communicate with external ICs, a 12-bit A/D Converter module for analog data acquisition, low-power mode, and on-chip Real-Time Clock/Calendar for keeping time while the device is otherwise asleep.

Transducer 46 is configured to transmit an acoustic signal externally of the housing of the monitoring device 12. In one embodiment, transducer 46 is a ceramic lead zirconate titanate (PZT) piezoelectric tube transducer having a width of 2.65 mm, an inner diameter of 1.8 mm, and an outer diameter of 2.54 mm and that is available as model 610HD from TRS Technologies Inc, USA. EPDM closed-cell foam may be inserted inside of transducer 46 to optimize the acoustic output of transducer 46. This transducer 46 configuration provides long range underwater wireless communication from the monitoring device 12 to the receivers of the system.

Transducer 46 is attached to circuit board 44 using a silver-filled epoxy (AA-DUCT 902) in one embodiment. A Parylene-C coating is applied to protect the circuit board 44 from moisture and also prevent potential shorts during handling and the assembly is encapsulated by an insulating epoxy using a flexible silicone mold to form the housing 40. Subsequently, ECG and EMG probes are attached and a final Parylene-C layer is applied to cover the surface of the entire device 12 to be waterproof and biocompatible in one embodiment.

As mentioned above, some embodiments of monitoring devices 12 are configured to monitor a plurality of different parameters including physiological and behavior parameters of the organisms as well as environmental parameters in illustrative embodiments. ECG and EMG circuitry may be provided to sense physiological parameters of the associated organism and generate outputs in the form of waveforms that may be processed to provide information regarding activity of the organism such as heart rate and muscle activity of the associated organism. Example behavior parameters that may be monitored include tail-beat frequency and activity level of the associated organism. Example environmental parameters that may be monitored include temperature, pressure and magnetic field.

Figure 4:
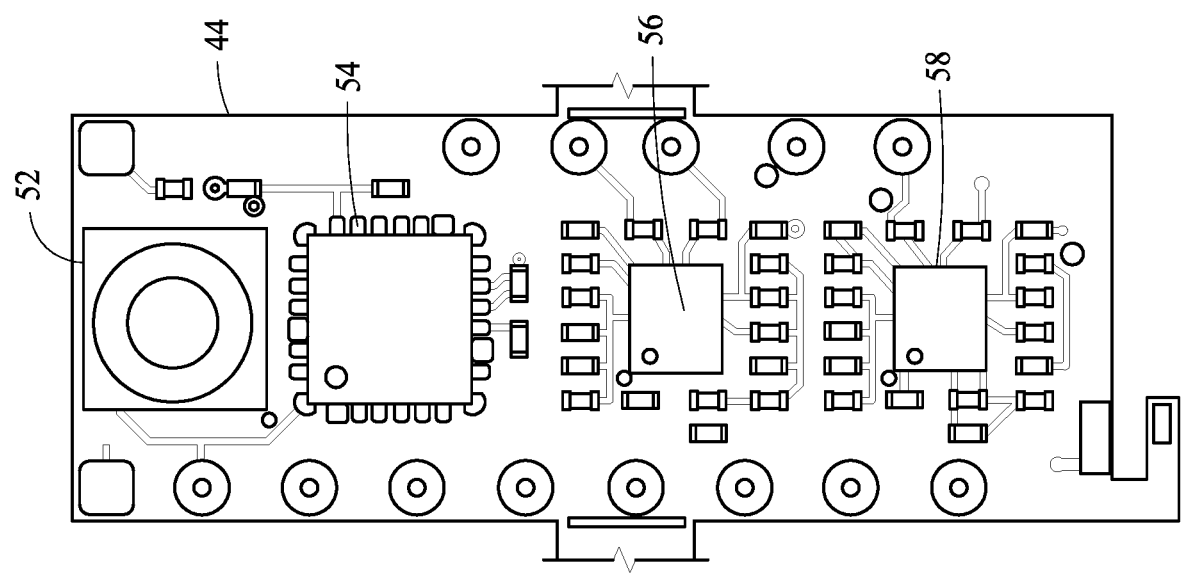
FIG. 4 is a plan view of a printed circuit board of a monitoring device according to one embodiment.

FIG. 4 shows an opposite side of the printed circuit board 44 of FIG. 3 and includes a pressure sensor 52, an inertial measurement unit (IMU) integrated circuit 54, electrocardiogram circuitry in the form of an ECG integrated circuit 56 and electromyogram circuitry in the form of an EMG integrated circuit 58. ECG IC 56 and EMG IC 58 are configured to generate respective electrocardiogram and electromyogram waveforms.

The circuitry and manufacture techniques described herein enable fabrication of monitoring devices 12 having a reduced form factor (e.g., a wet weight of 0.8 g and dimensions of 5.5 mm×6.5 mm×37 mm) that substantially reduces the adverse effects of implantation and tag burden to remain useful for small organisms.

Figure 5:
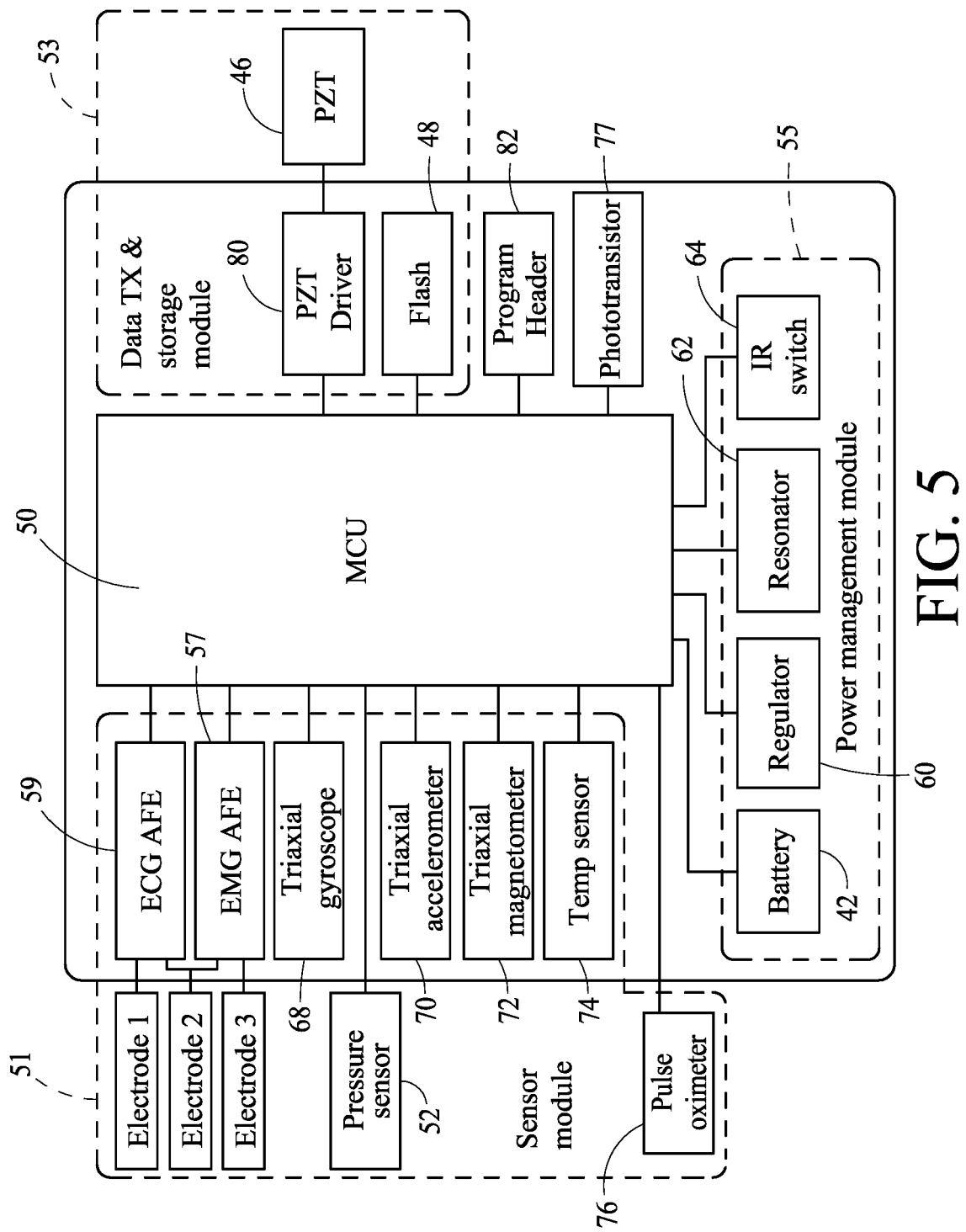
FIG. 5 is a functional block diagram of a monitoring device according to one embodiment.

Referring to FIG. 5, a functional block diagram of one embodiment of a monitoring device 12 is shown. The illustrated monitoring device 12 includes microcontroller 50 and a plurality of modules including a sensor module 51, a data, transmission and storage module 53, and a power management module 55. A modular design according to some embodiments of the disclosure permits customizability, upgradability, and reusability of the developed system for future use.

Sensor module 51 includes a plurality of sensors configured to monitor various parameters regarding the associated organism and/or environment. The sensors of the sensor module 51 generate outputs regarding one or more environment parameters in which the organism swims as well as outputs regarding physiological and behavioral parameters of the organism.

In one more specific embodiment, sensor module 51 includes environmental circuitry configured to sense at least one environmental parameter of the environment of the aquatic organism and generate an output indicative of the at least one parameter in one embodiment. In one more specific embodiment, the environmental circuitry includes a temperature sensor 74, a pressure sensor 54 and triaxial magnetometer 72 configured to sense temperature, pressure and magnetic field of an aquatic environment of the aquatic organism.

Sensor module 51 also includes behavioral circuitry configured to sense at least one behavioral parameter of the aquatic organism and generate an output indicative of the at least one parameter in one embodiment. In one more specific embodiment, the behavioral circuitry includes a triaxial gyroscope 68 and a triaxial accelerometer 70 configured to sense rotational and translational movements of the aquatic organism.

The illustrated example sensor module 51 also includes physiological circuitry configured to sense at least one physiological parameter of the aquatic organism and generate an output indicative of the at least one parameter in one embodiment. In one more specific embodiment, the physiological circuitry includes a pulse oximeter 76 as well as ECG and EMG circuitry discussed below with respect to FIGS. 14-15.

Figure 8:
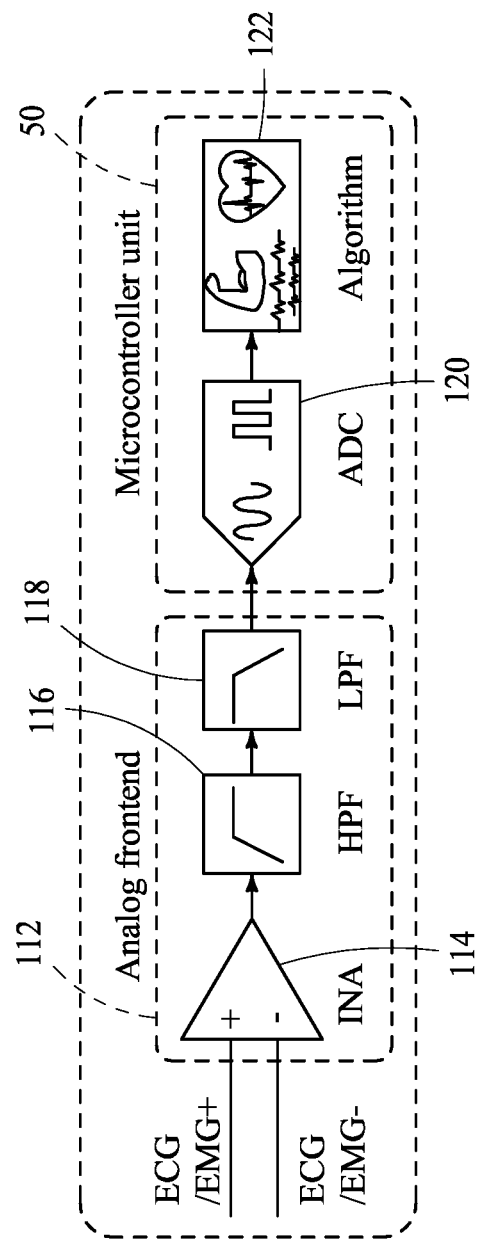
FIG. 8 is a schematic illustration of front-end data acquisition circuitry and processing circuitry of a monitoring device according to one embodiment.

In the illustrated embodiment, sensor module 51 may encompass off-the-shelf ICs and circuitry employing analog frontend (AFE) circuits 57, 59 for receiving respective outputs regarding physiological parameters of the aquatic organism, such as EMG, ECG waveforms. An example circuit implementation of analog frontends 57, 59 is shown in FIG. 8. Sensor module 51 further receives outputs from the sensors regarding monitored behavioral parameters of the aquatic organism (e.g., rotational and translational movements of the aquatic organism that may be used to calculate tail-beat frequency and activity level of the organism) as well as the ambient environment (e.g., temperature, pressure, and magnetic field).

Pulse oximeter 76 is an optical sensor that is configured to monitor physiological parameters of the organism such as arterial blood oxygenation, pulse rate, and the heartbeat of the organism by directing light into the subject and then detecting the scattered, reflected, or transmitted light. The pulse oximeter 76 may be used in and alternative or in addition to electrocardiogram (ECG) for monitoring heartbeat in one embodiment. The output of the pulse oximeter 76 is different from biopotential (i.e., electrical signal) measurement-based ECG and the pulse oximeter measures changes of the oxygen saturation level in the blood using a LED and photodiode to estimate the heart rate. Pulse oximeter 76 is implemented using part number BH1792GLC available from Rhom Semiconductor in one embodiment.

In addition, the pulse oximeter 76 does not require the probe to be implanted near the heart of the tagged animals as used in ECG monitoring. On the contrary, the pulse oximeter 76 may be implanted where there is blood flow in the organism which enables increased flexibility in implantation and tagging of the organism.

Microcontroller 50 is configured to process one or more of outputs generated by the environmental, behavioral, and physiological sensors to generate information regarding one or more environmental parameter, one or more behavioral parameter, and one or more physiological parameter of the aquatic organism. The generated information and/or raw data outputted by the environmental, behavioral, and physiological sensors may be transmitted externally of the device 12. Additional details regarding example processing and transmission are discussed below.

Phototransistor 77 is configured as an optical link to receive optical commands from a user, such as interrupts, and output the commands to the microcontroller 50.

Figure 16:
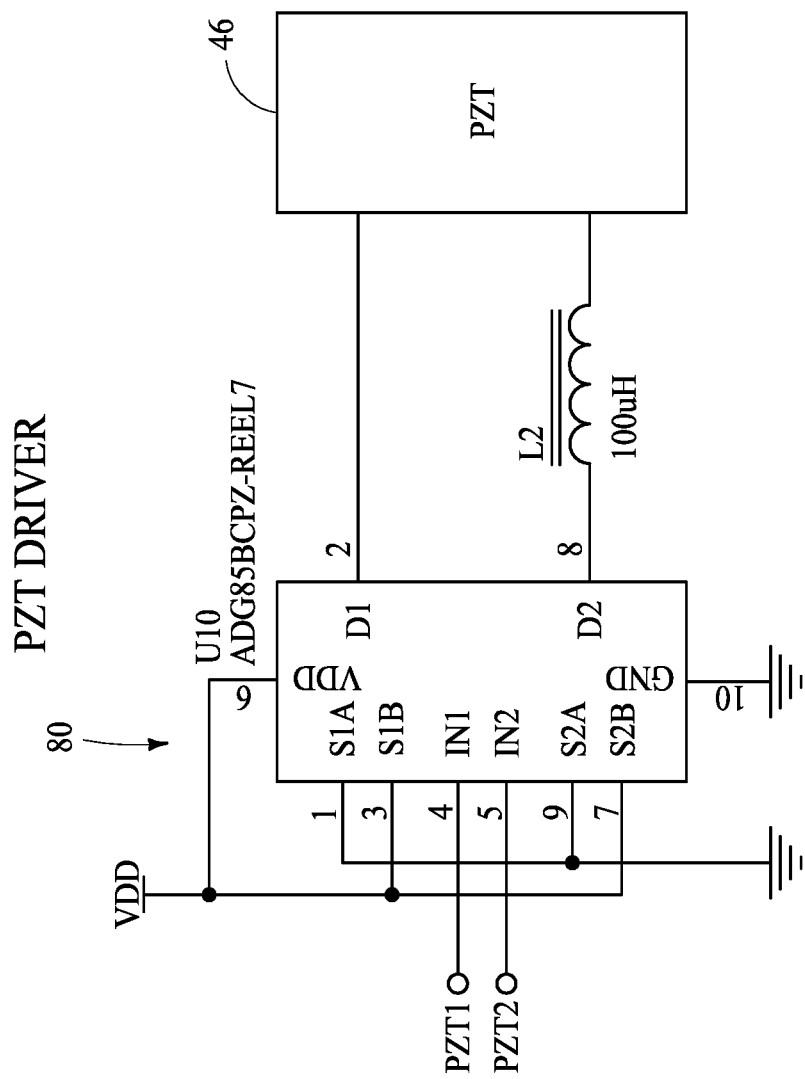
FIG. 16 is a circuit diagram of a PZT driver circuit of a monitoring device according to one embodiment.
Figure 8:
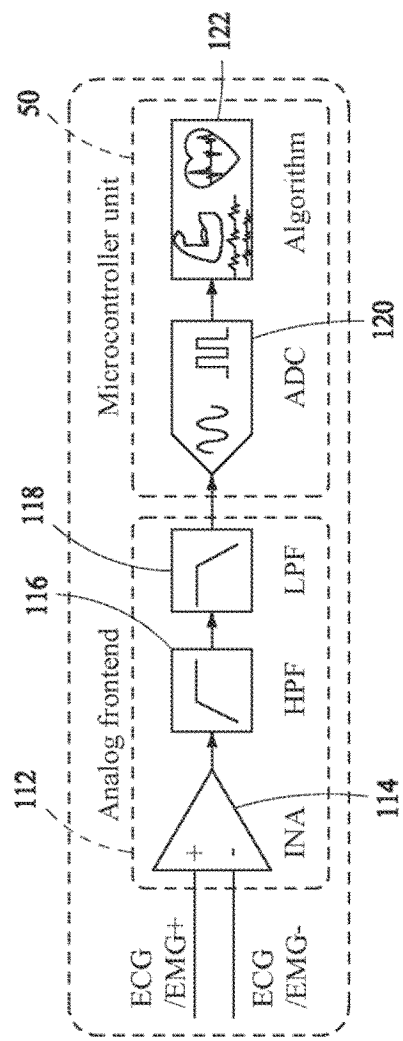
Figure 9:
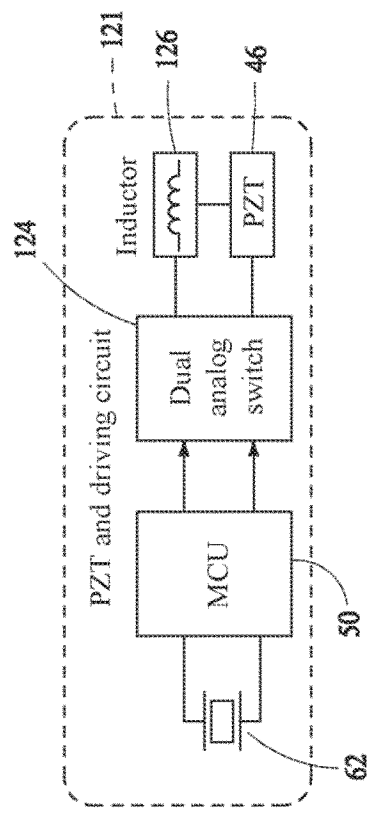

Data TX and storage module 53 includes a PZT driver circuit 80, flash memory 48 and a program header 82 in the illustrated embodiment. An embodiment of PZT driver circuit 80 is shown in FIG. 16. In one more specific embodiment, flash memory 48 is implemented as an 8-megabyte nonvolatile flash memory with 20-year data retention to store raw sensor data for further advanced signal processing after recovering the monitoring device 12.

Program header 82 is configured to load system firmware for the device 12.

Power management module 55 includes battery 42, a voltage regulator 60, resonator 62, and Infrared (IR) switch 64. The power management module enables a low-power operating system (e.g., 8 microamperes during system sleep) by combining hardware and software optimization techniques.

Battery 42 may be implemented as a lithium carbon fluoride battery of a similar design to that described in U.S. application Ser. No. 14/014,035, the teachings of which are incorporated herein by reference. Each laminate may include an anode and a cathode positioned between polymer separators that electrically isolate the cathode from the anode in the laminate. The separator may include microporous polypropylene. The cathode may include, or be constructed of, e.g., carbon fluoride and a conducting carbon within a binder affixed at a selected thickness to a current collector. The binder may include, e.g., polytetrafluoroethylene (PTFE). The anode may be constructed of lithium metal. The power source may be filled with an electrolyte such as, e.g., lithium hexafluorophosphate (LiPF6) disbursed in a selected volume ratio of ethylene carbonate (EC) and dimethyl carbonate (DMC). One embodiment of a suitable battery 42 is a lithium/carbon fluoride (Li/CFX) microbattery having an outer diameter of 4.8 mm, a length of 14.9 mm, weight of 380 mg, an open-circuit voltage greater than 3.2 V, volumetric energy density of at least 528 Wh/L, a capacity of up to 60 mAh, a peak output current up to 50 mA and a wide operating temperature range (−5° C. to 25° C.). Additional details are discussed in Wang, Y.; Liu, B.; Li, Q.; Cartmell, S.; Ferrara, S.; Deng, Z. D.; Xiao, J.; *Lithium and lithium ion batteries for applications in microelectronic devices: A review*; Journal of Power Sources 2015, pp. 286, 330-345, the teachings of which are incorporated herein by reference.

Voltage regulator 60 is configured to stabilize the power supply of the system and minimize output current supplied by the battery 42. In one embodiment, voltage regulator 60 is implemented using a DC/DC converter having part number LTC3525-5 available from Linear Technology Corporation Resonator 62 is configured to provide a stable and precise clock signal to monitoring device 12. In one embodiment, a 10 MHz clock signal is utilized.

Infrared switch 64 is used as the receiving interface to wirelessly program the monitoring device 12, such as activating or changing the pulse rate interval (PRI) of the device 12.

Figure 6:
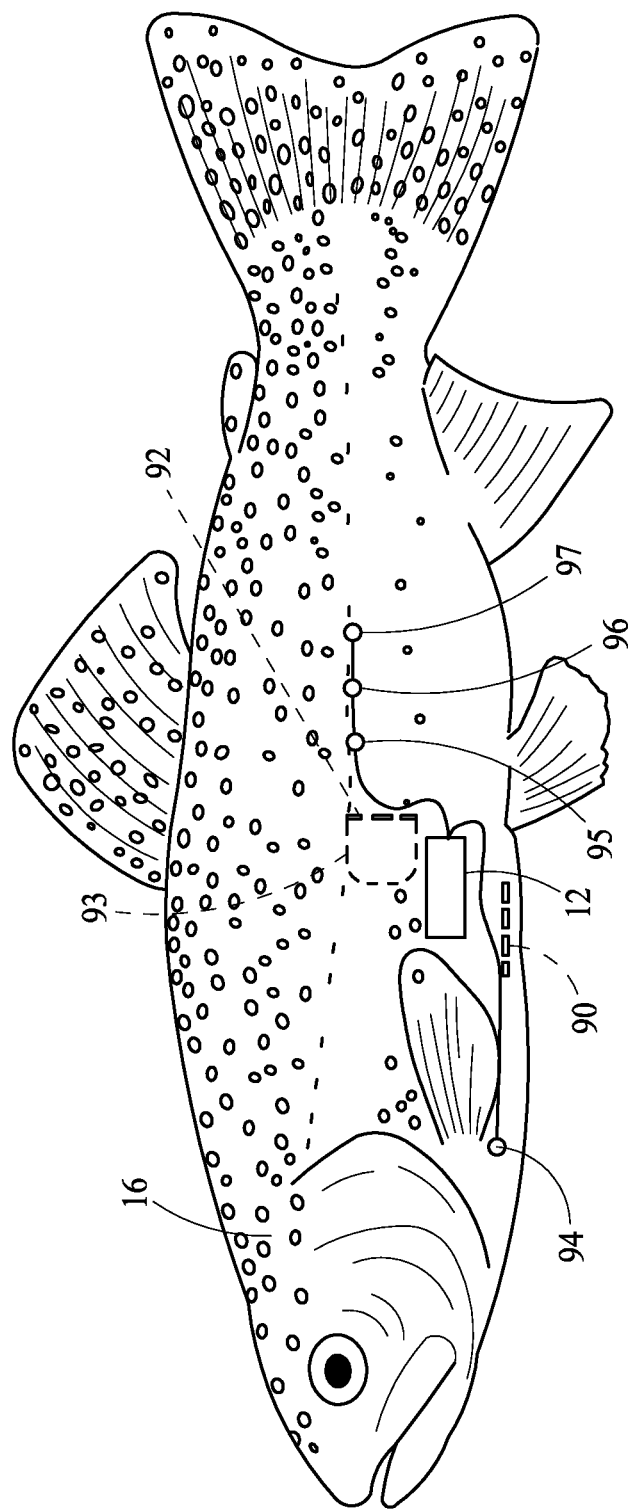
FIG. 6 is an illustrative representation of surgical implantation of a monitoring device within an aquatic organism according to one embodiment.

Referring to FIG. 6, one example embodiment of surgical implantation of a monitoring device 12 within the respective tagged organism 16 is described according to one embodiment. In this implementation, a horizontal incision 90 and vertical incision 92 are made in the organism 16. Horizontal incision 90 into the body cavity is administered along the linea alba (abdominal midline), halfway between the pectoral fins and pelvic fins. Horizontal incision 90 is made to provide access for placement of the ECG+ probe 94. Vertical incision 92 is made into the body cavity on the side of the organism 16, below the dorsal, and below the lateral line.

An ECG+ probe 94 is embedded subdermally into the tissue just ventral of the pectoral fins near the heart. ECG+ probe 94 is passed from vertical incision 92 through the body cavity of the organism 16 and out of the horizontal incision 90 using a sterilized 1.5 mm stainless steel tube, where the tip of the probe 94 is placed inside of the tip of the tube and the tube is used to support and provide rigidity for the wire to pass through the body cavity. The ECG+ probe 94 is then placed subdermally so that the probe is subdermally embedded in the musculature between the pectoral fins, near the heart.

Once the ECG+ probe 94 is affixed, the EMG+ probe 95, ECG− probe 96 and EMG− probe 97 are subdermally embedded into the side of the fish, through the incision 92, posterior to the incision 92. The EMG+ probe 95, ECG− probe 96 and EMG− probe 97 are affixed subdermally 1 cm apart near the lateral line and above the pelvic fin of the organism 16, and the monitoring device 12 is inserted into the body cavity of the organism 16 via vertical incision 92. Pulse oximeter 76 is placed in a subdermal pocket 93. The incisions 90, 92 are closed using one to three interrupted sutures (2×2×2×2) each.

Figure 7:
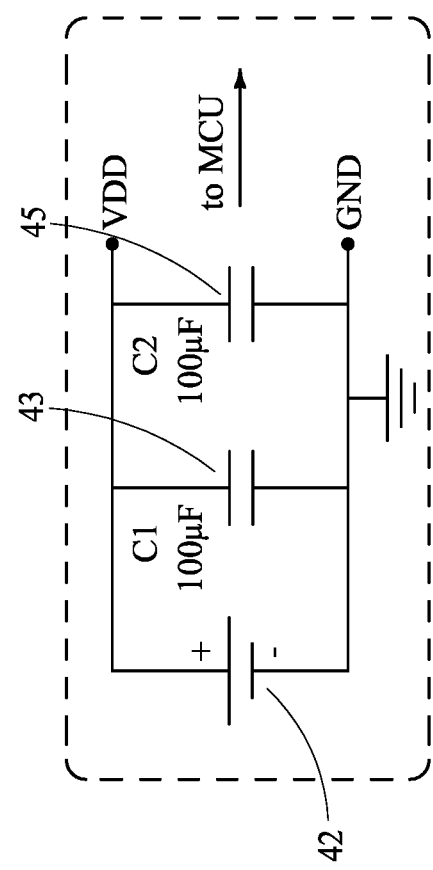
FIG. 7 is a schematic illustration of a power supply circuit of a monitoring device according to one embodiment.

Referring to FIG. 7, one embodiment of a power supply circuit 41 of a monitoring device is shown according to one embodiment. The power supply circuit 41 includes battery 42 and plural decoupling capacitors 43, 45 that provide operational energy to microcontroller 50 and other circuit components of device 12. A relatively high inrush current (e.g., up to 20 mA) occurs upon system wake up to charge the capacitors 43, 45 and other circuitry of the device 12. There is a relatively small instantaneous voltage drop of 0.15 V due to the low internal impedance of the battery 50 and this relatively small voltage drop ensures sufficiently high voltage can be continuously supplied to the device 12 providing normal operation.

Monitoring device 12 is configured as a low-power system by combining hardware and software optimization techniques in one embodiment. For example, to reduce the overall dynamic power, the microcontroller 50 is programmed to run at its full operational speed of 10 MHz because the fixed bias current becomes a negligible portion of the power consumption at higher frequencies. To reduce static power, the microcontroller 50 may be placed in retention sleep mode with all the sensors disconnected using an N-channel enhancement mode field-effect transistor. In addition, all the bidirectional I/O pins of the MCU 50 may be configured as an output pin driving to low, or input pulled to VSS to ensure that they are not floating. Furthermore, only the currently needed features were enabled at any point during operation and longer pulse rate intervals may be used providing less frequent data acquisition and transmission and thereby extending the life of the monitoring device 12.

Referring to FIG. 8, one embodiment of analog front-end (AFE) circuits 57, 59 implemented as a biopotential acquisition circuit is illustrated to extract, amplify, and filter small biopotential signals from probes 94-97 in the presence of noise. The described biopotential signal acquisition circuit employs biocompatible and corrosion-resistant stainless-steel needle probes.

The acquired signals are primarily conditioned by an analog frontend (AFE) 112 that includes an instrumentation amplifier (INA) 114 which amplifies the input signals with a gain of 100×. The amplified signals are provided to a two-pole, high-pass filter 116 for eliminating motion artifacts and the electrode half-cell potential in conjunction with a Sallen-Key filter topology as the secondary low-pass filter 118 to remove line noise and other interference signals and provides an additional gain of 11×. The passband of the circuitry has been configured to 23.4 to 514 Hz with a quality factor of 0.8 for the EMG circuit 56, and 7 to 25 HZ with a quality factor of 1 for the ECG circuit 58, respectively. Both systems exhibit an overall gain of 1100× in the described example embodiment.

The conditioned signals are subsequently sampled by the analog-to-digital converter (ADC) 120 of the microcontroller unit 50 at 100 Hz for storage and/or further onboard data processing in one embodiment.

Outputs of the ECG and EMG circuitry are processed to provide information regarding heartbeats and muscle activity of the organism in one embodiment. ECG and EMG algorithms 122 described below may be executed by the microcontroller 50 to process the sampled data as discussed in detail below. In one embodiment, algorithms 122 are implemented with integer arithmetic for execution and operation in real-time without requiring excessive computational power and allowing real-time transmission of the physiological data.

In one example, the ECG processing results in a clear QRS profile from the ECG waveform, and the QRS complex of the ECG waveform is associated with the functioning of the heart of the organism. A measured heart rate difference is correlated to a combination of parameters, including species, ambient environment, external stimulus, and history of behavior.

In one embodiment, real-time ECG peak detection algorithm is based on Pan-Tompkin's real-time QRS detection algorithm described in Pan, J.; Tompkins, W. J.; A real-time QRS detection algorithm, IEEE Trans. Biomed. Eng, 1985, 32 (3), pp. 230-236, the teachings of which are incorporated herein by reference.

The ECG data processing may extract the heart rate from fractions of 6-seconds of raw ECG data. The 6-second data acquisition period covers possible heart rates down to 20 BPM. The ECG processing includes a sequence of processing steps including filtering, differentiation, amplitude squaring, moving-window integration, and discrimination of the QRS complex in one embodiment.

In one more specific embodiment, the ECG circuitry is enabled to sample 6-second raw data at 100 Hz. The raw data is smoothed and the derivative is determined to provide QRS complex slope information and the derivative is squared to eliminate the negative slope. Thereafter, an integration with a moving window of eight points is calculated and when the integration changes rapidly and is larger than a threshold, the point is considered a peak candidate. The peak candidate is compared with an updated threshold, the current slope is compared to the slope of the previous peak and it is determined whether the RR interval between QRS complexes is within a 200 ms to 360 ms range. If the peak candidate satisfied all these conditions, it is considered a peak in one embodiment. The algorithm automatically adjusts thresholds, RR interval average, and other parameters periodically. If no peaks are detected for a predefined time, it will perform a back search and update the thresholds and RR intervals to allow for lower signals to be detected. The final RR interval for the 6-second period is used to obtain the heart rate of the organism in the described embodiment. Experiments on rainbow trout in vivo verified that the above example processing detects ECG peaks in real-time with a 99.4% accuracy.

In one embodiment, the real-time EMG algorithm calculates the intensity of muscle activities of the organism and is based upon the algorithm discussed in Kaseloo, P. A., et al., A Biotelemetry System For Recording Fish Activity, *Journal of Fish Biology*, vol. 40, issue 2, February 1992, pp. 165-179, the teachings of which are incorporated herein by reference. Voltage oscillations observed around half of the peak voltage in the EMG waveform are associated with axial musculature contraction of the organism.

In particular, the onboard EMG data processing algorithm performs integration of a 6-second window of raw EMG data to an EMG index that represents the intensity of muscle activities. The 6 seconds of EMG raw data is recorded with a sampling frequency of 100 Hz simultaneously with ECG recording to reduce the total data acquisition period and power consumption. A baseline voltage, around which the EMG signal fluctuates, is first determined and a typical baseline value is around ½ VDD. The function calculates the absolute difference from each data point to the baseline and sums the absolute differences over the period of 6 seconds. Finally, the sum is divided by a reference value to yield an EMG index between 0 to 255, where 0 denotes no muscle activity, and 255 denotes extremely intense muscle activity of the organism.

As discussed above, monitoring devices 12 are also configured to monitor behavior of aquatic organisms according to some embodiments. Example behavioral parameters that may be monitored include tail-beat activity and activity level of the tagged organism. For example, the monitoring device 12 discussed herein includes an inertial measurement unit that includes a plurality of motion sensors (triaxial gyroscope 68 and triaxial accelerometer 70). The outputs of either of the gyroscopes or accelerometers may be used to determine tail-beat frequency and activity level. Different behavior patterns of the organism are distinguished by processing the outputs of the motion sensors, including relaxing, startle, swimming, burst swimming, speeding up, and stopping. Data processing algorithms executed by the microcontroller 50 convert raw motion sensor data regarding the behavioral parameters to information regarding fish behavior including tail-beat frequency and level of activity of the organism.

In one embodiment, the accelerometers 70 of the monitoring device 12 record surging motion in the direction of the main axis of the organism (forward and backward), swaying motion along the axis crossing the animal body (side to side), and heaving motion on the vertical axis of the body (up and down) in one embodiment.

In another embodiment, angular velocities from the gyroscopes 68 are utilized instead of acceleration since the gyration measurement is more sensitive and more accurate than the acceleration and angular velocities normally oscillate around zero during swimming and are thus more suitable for detection than accelerations.

As mentioned previously, the monitoring device 12 is configured to generate information indicative of the tail-beat frequency of an associated organism and the tail-beat frequency may be correlated to swimming speed of the organism. In one embodiment, the microcontroller 50 extracts frequency domain features from three-dimensional (3D) angular velocities of the gyroscopes 68 through fast Fourier transform (FFT) analysis on account of the swimming motion periodicity. FFT analysis is applied to the periodic patterns of the motion signals obtained from the dynamic behavior of the organism and the obtained spectrum enables the tail-beat frequency (TBF) to be determined and that is related to swimming speed of the tagged organism being monitored. In one more specific embodiment, the tail-beat frequency is obtained from each axis after FFT analysis and the tail-beat frequency is determined by the most sensitive axis.

The microcontroller 50 is configured to determine a level of activity of the organism in one embodiment. In one implementation, the activity level is calculated through an integration of a 6-second window of data from the triaxial gyroscopes. Integration over a 6-second period of data per axis allows the overall dynamic body activity to be determined. The X, Y, and Z components from the triaxial gyroscopes are summed to provide a unitless level of activity parameter over time with respect to the organism.

Figure 9:
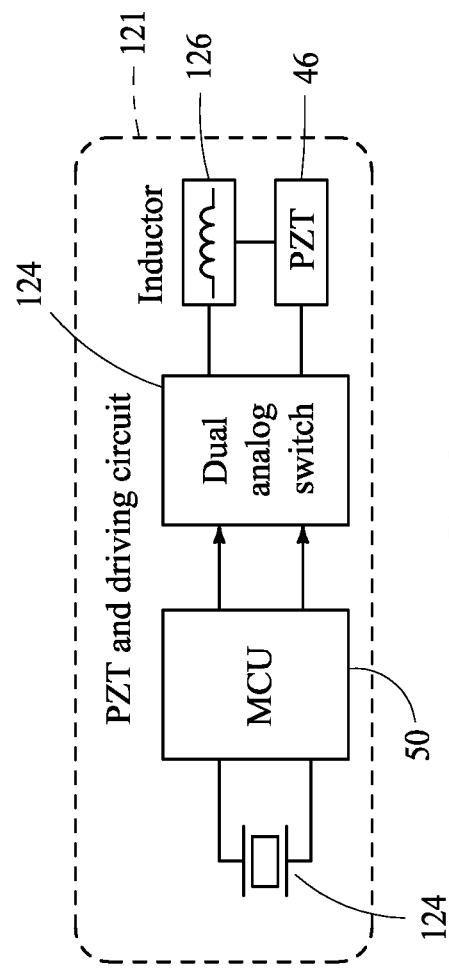
FIG. 9 is a schematic illustration of drive circuitry and an acoustic transducer of a monitoring device according to one embodiment.

Monitoring device 12 utilizes acoustic waves for underwater wireless communication according to some embodiments of the disclosure. Referring to FIG. 9, one embodiment of an acoustic communication module 121 is shown including a tube piezoelectric transducer 46 and associated drive circuitry including a resonator 122, microcontroller 50, a dual analog switch 124 and an inductor 126. The illustrated drive circuitry corresponds to the PZT driver circuit 80 of FIG. 5 in one embodiment.

In one embodiment, the dimensions and geometry of the transducer 46 were designed to achieve a hoop-mode resonance frequency of 416.7 kHz, which is beyond the background noise in turbulent aquatic environments, and to achieve an omnidirectional acoustic beam pattern. During operation, the driving circuit outputs a binary phase-shift keying (BPSK) encoded waveform through analog switch 124 onto either side of the transducer 46 to generate time-critical signals at 416.7 kHz. The acoustic waveform includes a 31-bit hexadecimal value comprising a 7-bit Barker code, a 16-bit payload including information regarding data collected from one or more sensors, and an 8-bit cyclic redundancy check (CRC) code in one embodiment.

The series inductor 126 is coupled with one electrode of the transducer 46 and establishes a resonance with the fundamental capacitance thereof. As a result, a much higher effective driving voltage of up to 15 V was achieved, leading to stronger signal strength, thus a longer transmission distance.

One embodiment of the transducer 46 is polarized in its wall thickness direction and vibrates radially and the acoustic signals are primarily radiated 360° from the wall surface of the transducer 46. The mean source level of the acoustic signal for the front 180 degrees of the monitoring device 12 is 156.3 dB which translates into a theoretical transmission range up to 400 meters. The emitted signal is blocked by the main body of the device 12 in a direction towards the rear and the source level is accordingly weaker in the rear direction.

Figure 10:
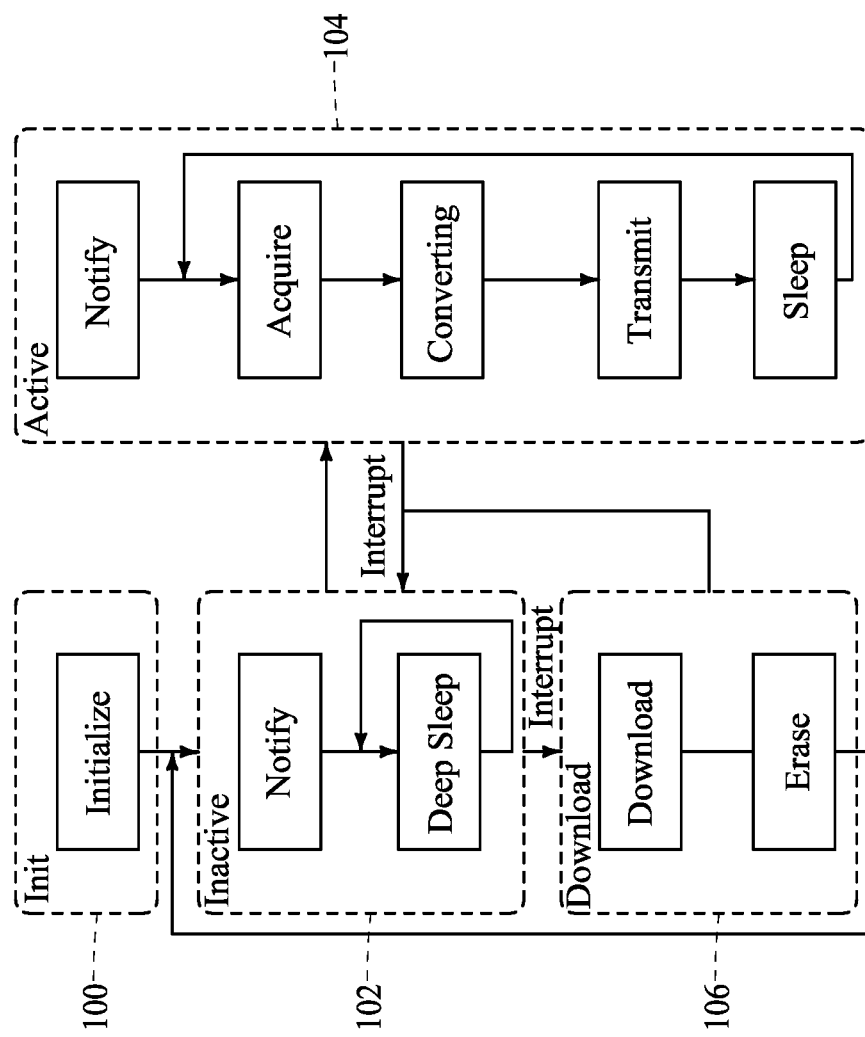
FIG. 10 is a flow chart of firmware executed by a monitoring device according to one embodiment.

Referring to FIG. 10, one embodiment of firmware implemented within the monitoring device is shown according to one embodiment. The illustrated firmware is a finite-state-machine model for performing control, monitoring, data manipulation, and wireless communication functions of monitoring device 12. At any point of time, the firmware is in one of the following four states: (i) initialization (Init) 100 state for software and hardware configuration, (ii) inactive (Inactive) state 102 whereby the system is programmed in a low power mode with all modules temporarily shut down, (iii) active (Active) state 104 for data acquisition, processing, and communication, and (iv) download (Download) state 106 for accessing the data from the onboard flash memory). A hardware interrupt triggers the firmware to switch to a different state.

The system starts up at the Init state 100 where the microcontroller 50 is initialized with software and hardware configuration. The firmware enters Init state 100 one-time unless a brown-out reset (BOR) occurs when the battery voltage drops below critical voltage requirement.

After the completion of the initialization step, the system enters the Inactive low-power sleep state 102 started by sending out a unique acoustic notification code (e.g., 30 repetitions of the tag code with a PRI of 1 s) to the user. The system is programmed in a low power mode (deep sleep) running from an internal low power RC oscillator (LPRC) clock source at 32 kHz with all modules 51, 53, 55 temporarily shut down except for the UART input, phototransistor input, which receives programmed optic interrupt signals, and the watchdog timer (WDT) module, which wakes up the system at a predefined time interval. The system will loop in the inactive state 102, maintaining a minimal power consumption, until an active signal is received from a user to enter download state 106, or the reception of optic interrupt signals via the phototransistor to command the system to enter active state 104.

Once an activation interrupt signal is received by the phototransistor, the system enters the active state 104 with the system switched to full mode based upon a high-speed and precise external resonator 124 operating at 10 MHz. The system enters the Active state and sends out the acoustic notification code to indicate the status change of the device (30 repetitions of the tag code with a PRI of 1 s) to the user. The sensors of sensor module 51 take turns for acquiring their respective data in one embodiment. For example, the microcontroller first reads motion data from the IMU at a sampling frequency of 1 kHz for ten data points. Next, the microcontroller reads the temperature and pressure from the respective sensors and thereafter reads physiological data from the pulse oximeter at a sampling frequency of 32 Hz for 5 sec within an interrupt routine until completed, and simultaneous EMG and ECG readings at a sampling frequency of 100 Hz for 6 s.

After completing the reading of data from the physiological, behavioral and environmental sensors, the full set of raw data is stored in the memory 48 in some embodiments. The data (e.g., raw ECG and EMG data, data from the IMU 54, and data from the environmental sensors) may be processed onboard by microcontroller 50 in a conversion act to reduce the amount of data to be transmitted via the transducer 46 in some embodiments. The microcontroller 50 may process the data in some embodiments to extract key physiological parameters from the continuous ECG and EMG time-domain waveforms and performs preliminary filtering to remove unwanted data and reduce the onboard memory use.

The data is transmitted externally of the device using the PZT 46 during the active state in one embodiment. Following data acquisition and processing, the firmware actuates the PZT 46 at a precise time for generating time-critical acoustic signals for acoustic communication of the data externally of the monitoring device. Thereafter, modules 51, 53, 55 are again shut down to conserve energy from the battery in one embodiment.

In some embodiments, data from one or more of the physiological, behavioral and environmental sensors (and/or information resulting from the processing thereof by microcontroller 50) may also be transmitted externally of the monitoring device via the PZT and processed by the management system.

Subsequently, the system enters the inactive state 102 until the next loop. The system can be interrupted in either the inactive state 102 or active state 104 to the download state 106 by connection of the device 12 to a host computer and raw data of the memory of the device may be downloaded to a host PC of a user. The data may be erased from the memory of the device as well. The user of the system has the options during the download state 106 of (1) print the version information of the firmware of the connected device; (2) download the data from the onboard flash with text format; (3) download the data from the onboard flash with binary format; (4) erase the flash memory, and (5) exit from download state to the inactive state.

The monitoring device 12 has the ability to hibernate (sleep) during the active state 104 for a user-specified length of time before the next loop of data acquisition, processing, and transmission starts to extend device longevity.

A communication protocol for reliable and robust transmission of time-variant acoustic signals is utilized to overcome the challenges in underwater acoustic communication associated with high path loss, time-varying propagation, and doppler spread along the channel. In one embodiment, the communication protocol is based on the transmission of a pulse train of multiplexed messages. The interval between each transmitted message is referred to as a pulse rate interval (PRI) and additional teachings thereof are set forth in Deng, Z.; Carlson, T. J.; Li, H.; Xiao, J.; Myjak, M. J.; Lu, J.; Martinez, J. J.; Woodley, C. M.; Weiland, M. A.; Eppard, M. B; *An injectable acoustic transmitter for juvenile salmon*; Scientific reports 2015, 5 (1), 1-6, the teachings of which are incorporated herein by reference.

Figure 11:
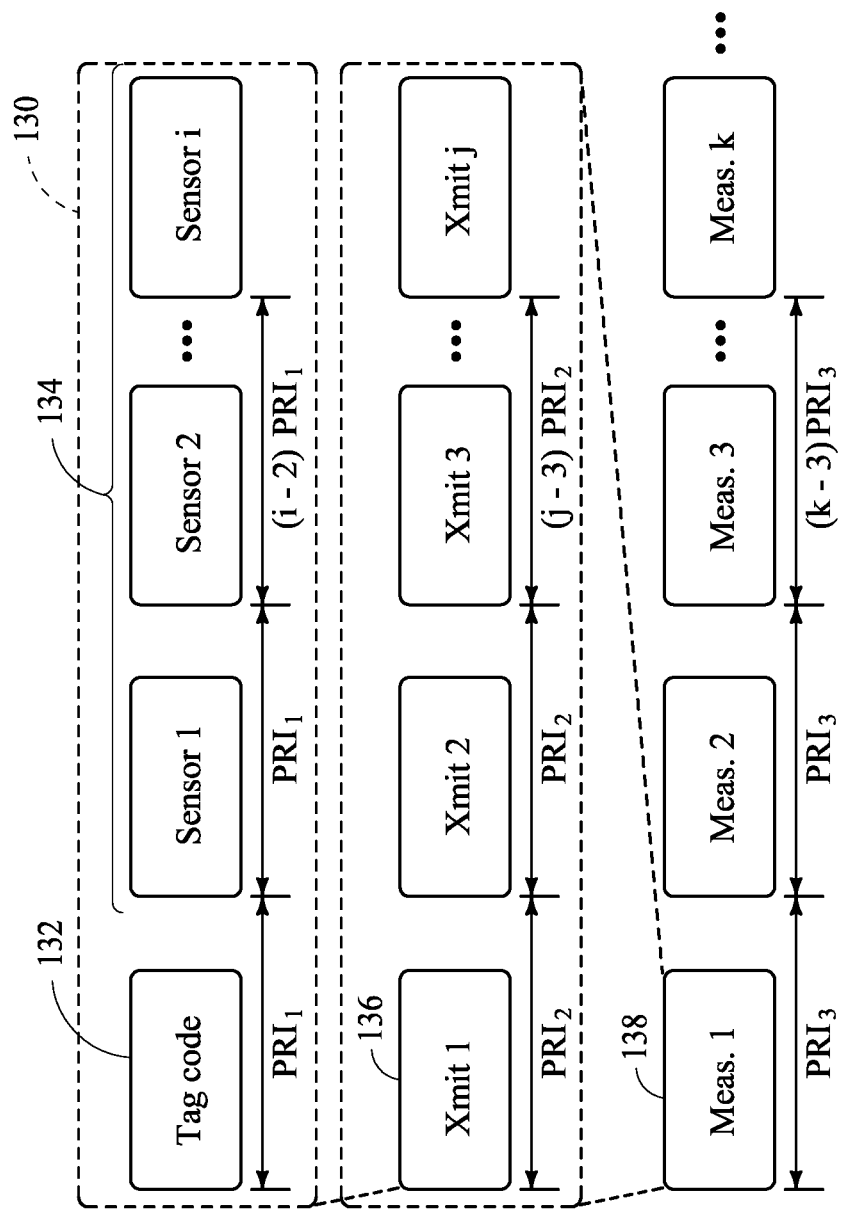
FIG. 11 is a schematic illustration of a timing protocol for time-variant acoustic data communication according to one embodiment.

Referring to FIG. 11, one example communication protocol 130 that may be utilized to transmit data externally of the monitoring device 12 is shown. The protocol 130 transmits 31-bit acoustic signals i+1 times with a first pulse rate interval PRI1. The first signal 132 contains the unique identification code (tag code) of the monitoring device and the following i signals 134 contain data from each of the sensors of the monitoring device including data from physiological, behavioral and environmental sensors or information resulting from the processing thereof. In one embodiment, data from each of the sensors is transmitted serially one after another in signals 134.

The above-described bundle of i+1 transmissions 136 is repeated for j times with a pulse rate interval PRI2 to permit the receiver to decode the transmitted tag code along with the sensor data from the monitoring device 12.

Another pulse rate interval PRI3 is used to denote the interval between each duration of new measurements 138 by the physiological, behavioral and environmental sensors of the device 12. Accordingly, the same data may be outputted from device 12 in a plurality of different transmissions 136.

Figure 12:
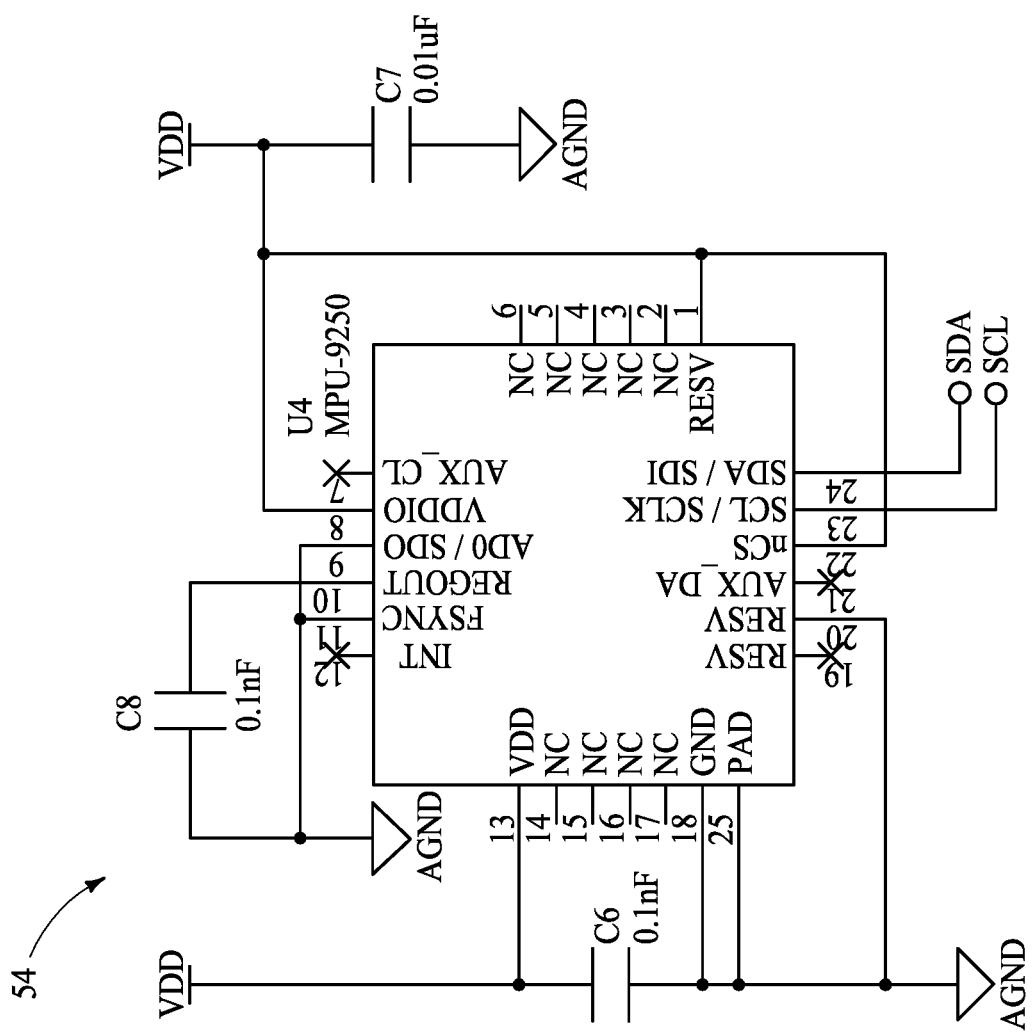
FIG. 12 is a circuit diagram of an inertial measurement unit of a monitoring device according to one embodiment.
Figure 13:
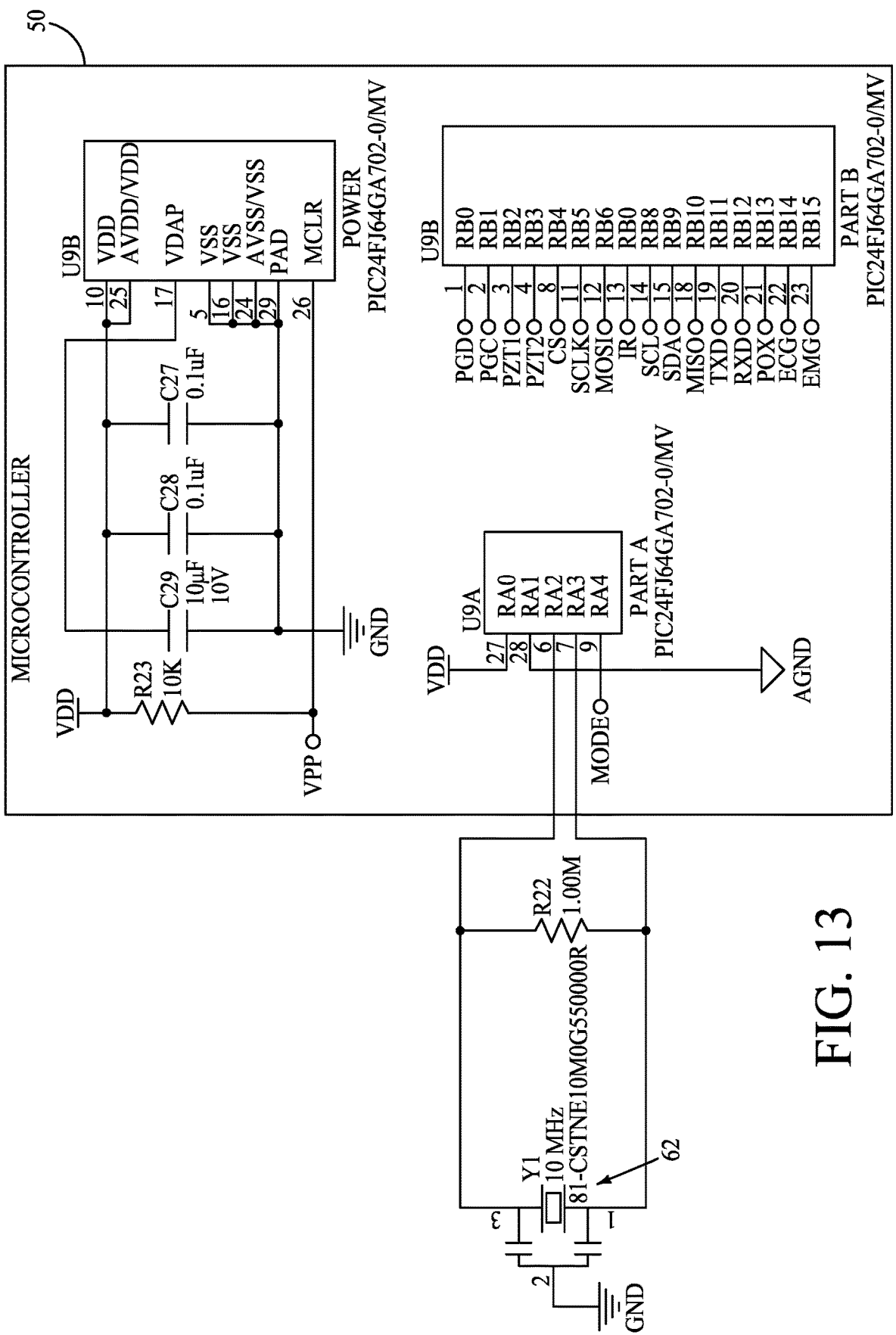
FIG. 13 is a circuit diagram of a microcontroller and a resonator of a monitoring device according to one embodiment.
Figure 14:
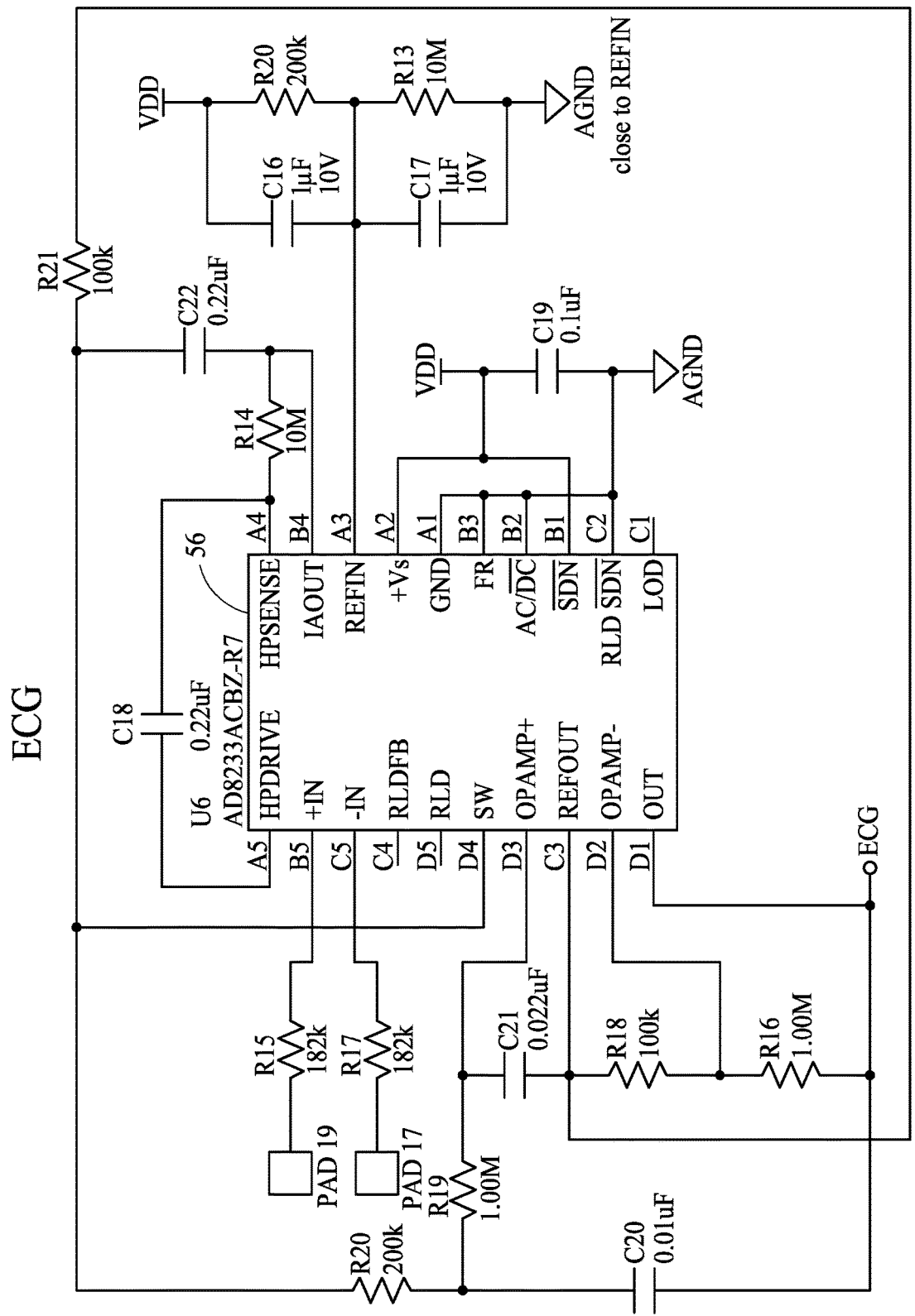
FIG. 14 is a circuit diagram of an electrocardiogram (ECG) circuit of a monitoring device according to one embodiment.
Figure 15:
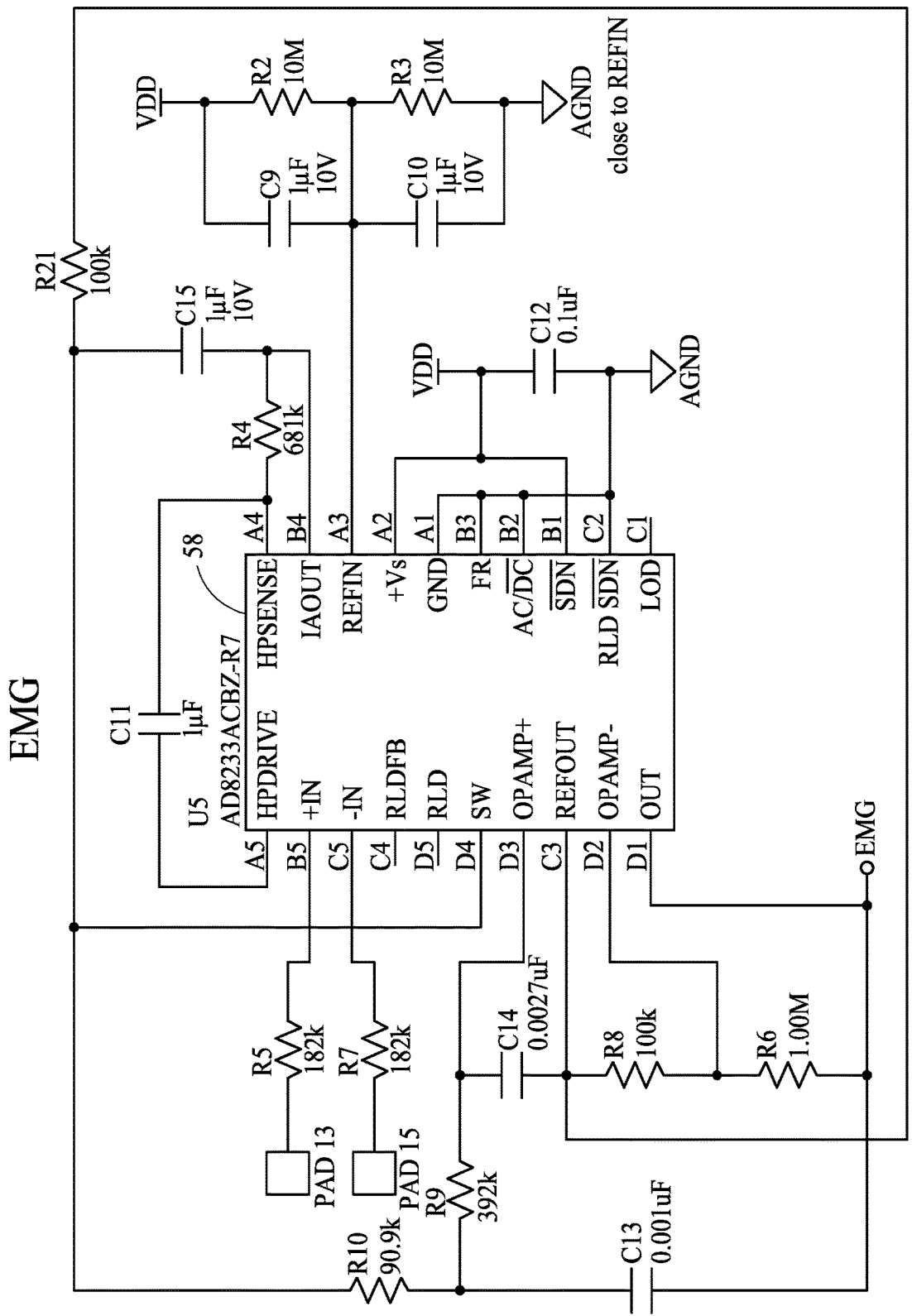
FIG. 15 is a circuit diagram of an electromyogram (EMG) circuit of a monitoring device according to one embodiment.

Referring to FIGS. 12-16, example circuitry of various components of monitoring device 12 is shown. FIG. 12 is a circuit diagram of a inertial measurement unit 54 according to one embodiment. FIG. 13 is a circuit diagram of a microcontroller 50 and a resonator 62 according to one embodiment. FIG. 14 is a circuit diagram of ECG circuitry include ECG IC 56 according to one embodiment. FIG. 15 is a circuit diagram of EMG circuitry including an EMG IC 58 according to one embodiment. FIG. 16 is a circuit diagram of a PZT driver circuit 80 according to one embodiment.

In one embodiment, ECG IC 56 and EMG IC 58 are each implemented using part number AD8233 available from Analog Devices, Inc. ECG IC 56 and EMG IC 58 output respective electrocardiogram and electromyogram waveforms that are received and processed by microcontroller 50. In one embodiment, the electrocardiogram waveform is processed to identify heart beats and heart rates of the aquatic organism and the electromyogram waveform is processed to quantify muscle activity of the aquatic organism.

In one embodiment, triaxial gyroscope 68, triaxial accelerometer 70, and triaxial magnetometer are implemented using the IMU IC 54. IMU 54 may be implemented using part number MPU-9250 available from InvenSense. This example IMU 54 is a multi-chip module (MCM) consisting of two dies integrated into a single QFN package. One die houses a 3-Axis gyroscope and the 3-Axis accelerometer and the other die houses a AK8963 3-Axis magnetometer from Asahi Kasei Microdevices Corporation providing a 9-axis motion tracking device that combines a 3-axis gyroscope, 3-axis accelerometer, 3-axis magnetometer and a digital motion processor in a small 3×3×1 mm package. In addition, the MPU-9250 IMU utilizes three 16-bit analog-to-digital converters (ADCs) for digitizing the gyroscope outputs, three 16-bit ADCs for digitizing the accelerometer outputs, and three 16-bit ADCs for digitizing the magnetometer outputs.

As discussed herein, some embodiments of the disclosure provide monitoring devices 12 that are configured to monitor physiological, behavioral and environmental parameters of an organism. In one embodiment, monitoring device 12 is configured to generate raw ECG and EMG waveforms that be analyzed using various analytic methods. For example, heart rate data of the organism may be derived from the generated ECG waveform, and muscle activity data may be derived from the EMG waveform.

Monitoring device 12 may also monitor behavioral parameters including tail-beat frequency that is correlated to swimming speed of the tagged organisms and an activity level that is correlated to the activity of the organism.

Examples environmental parameters that may be monitored include temperature, pressure and magnetic field of the environment of the organism.

The different parameters being monitored may be correlated with one another to learn information regarding the organism within its environment. For example, a change in heart rate could be due to a sudden temperature change, a natural change due to day/night pattern, or a sudden increase of the activity level (due to various reasons). Only looking at the heart rate of the tagged organism would not provide information regarding what caused the change of the heart rate, and would not be possible to predict how the heart rate will be. On other hand, only measuring the temperature of the environment would also not predict how the heart rate trend will be in the future since other parameters need to be considered. The environmental, behavior, and physiological monitoring capabilities of some embodiments disclosed herein enable additional information regarding organisms to be determined from the correlation of the data that is not possible with conventional monitoring devices and allows more complete understanding of causes and the future trend of physiology and behavior. Furthermore, the monitoring devices serve as a mobile sensing platform of the environment. The data generated for the different parameters allows an increased understanding from a larger perspective of aquatic animal ecology, social behavior, and environmental impact.

The data of the different parameters may be associated or correlated with respect to each other. For example, the parameters may be graphed with respect to one another and aligned with respect to time in one example of data correlation and that permits analysis of the physiological and behavioral parameters with respect to environmental parameters. In another example, heart rates of the organisms may be graphed relative to temperature over time allowing impacts of temperature on heart rate to be studied. In another example, the activity level of the organisms may be graphed relative time of day that permits day-night rhythm analysis. The monitoring of real-time environmental parameters including temperature, pressure, and magnetic field and the resultant data may be used to understand the behavior of the organisms and provide additional insight regarding physiology.

Monitoring devices 12 described herein provide an abundance of features with device longevity while maintaining a comparable or even smaller form factor than other commercially available devices. The example monitoring devices 12 described herein permit biologists and ecologists to apply a wider range of sensors and study smaller species for a longer duration of time, which has not been possible with existing devices.

Three distinct fish species, rainbow trout, walleye, and sturgeon were studied to validate the functionality and effectiveness of the implanted monitoring devices. In vivo real-time physiology, behavior, and environmental monitoring capabilities not only enabled quantification of the ambient conditions, physiology, and activity patterns, but also allowed correlation of physiological response with environmental stimulus or cumulated behavior. The combination of features of the monitoring devices disclosed herein enables ecologists to continuously monitor most aspects of an aquatic animal's behavior and physiology (e.g., location, locomotion, caloric expenditure, interactions with other animals) and enable the use of animals as sensors of the environment (e.g., temperature, salinity, depth), and provide insight regarding physiology, behavior, and ecology of wild aquatic animals in situ at challenging locations that would have previously been limited to tests on model organisms in highly controlled settings, due to device limitations.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended aspects appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

What is claimed is:

1. An aquatic organism monitoring device comprising:
a housing configured to be physically associated with an aquatic organism;
environmental circuitry coupled with the housing and configured to generate a first output indicative of at least one environmental parameter of an environment of the aquatic organism;
behavioral circuitry coupled with the housing and configured to generate a second output indicative of at least one behavioral parameter of the aquatic organism;
physiological circuitry coupled with the housing and configured to generate a third output indicative of at least one physiological parameter of the aquatic organism;
a transmitter coupled with the housing and configured to transmit a signal externally of the housing while the housing and the transmitter are physically associated with the aquatic organism, and wherein the signal includes information regarding one or more of the at least one environmental parameter of the environment, the at least one behavioral parameter of the aquatic organism, and the at least one physiological parameter of the aquatic organism;
wherein the behavioral circuitry is configured to generate the second output indicative of the at least one behavioral parameter comprising movement of the aquatic organism; and
processing circuitry configured to process the second output to generate the information regarding the at least one behavioral parameter of the aquatic organism comprising a tail-beat frequency of the aquatic organism.

2. The monitoring device of claim 1 wherein the processing circuitry is configured to process the first and third outputs to generate the information regarding the environmental parameter and the physiological parameter of the aquatic organism.

3. The monitoring device of claim 2 wherein the processing circuitry is configured to process the third output to identify a plurality of peaks to generate the information regarding the at least one physiological parameter comprising heart rate of the aquatic organism.

4. The monitoring device of claim 2 wherein the processing circuitry is configured to process the third output to generate the information regarding the at least one physiological parameter of the aquatic organism indicative of musculature contractions of the aquatic organism.

5. The monitoring device of claim 2 wherein the processing circuitry is configured to process each of the first, and third outputs to generate the information regarding each of the at least one environmental parameter and the at least one physiological parameter, and wherein the information regarding the at least one environmental parameter, the information regarding the at least one behavioral parameter, and the information regarding the at least one physiological parameter are correlated with respect to one another and with respect to time.

6. The monitoring device of claim 1 wherein the environmental circuitry is configured to generate the first output indicative of the at least one environmental parameter including one or more of temperature, pressure, and magnetic field of the environment of the aquatic organism.

7. The monitoring device of claim 6 wherein the housing is configured to be inserted into a body of the aquatic organism.

8. The monitoring device of claim 1 wherein the behavioral circuitry comprises a triaxial gyroscope configured to generate the second output indicative of the at least one behavioral parameter comprising rotations of the aquatic organism about three axes.

9. The monitoring device of claim 8 wherein the housing is configured to be inserted into a body of the aquatic organism.

10. The monitoring device of claim 1 wherein the physiological circuitry comprises electrocardiogram circuitry configured to generate the third output comprising an electrocardiogram waveform indicative of heart beats of the aquatic organism.

11. The monitoring device of claim 1 wherein the physiological circuitry comprises electromyogram circuitry configured to generate the third output comprising an electromyogram waveform indicative of muscle activity of the aquatic organism.

12. The monitoring device of claim 1 wherein the physiological circuitry comprises a pulse oximeter, and wherein the third output is indicative of heart beats of the aquatic organism.

13. The monitoring device of claim 1 wherein the signal includes the information regarding each of the at least one environmental parameter, the at least one behavioral parameter, and the at least one physiological parameter.

14. The monitoring device of claim 1 wherein the signal includes the information regarding the at least one environmental parameter.

15. The monitoring device of claim 1 wherein the signal includes the information regarding the at least one environmental parameter, and wherein the processing circuitry is configured to process the first output to generate the information regarding the at least one environmental parameter that is included in the signal that is transmitted.

16. The monitoring device of claim 1 wherein the first output is devoid of information regarding location of the aquatic organism monitoring device and is devoid of information regarding location of the aquatic organism.

17. The monitoring device of claim 1 wherein the aquatic organism is within water of the environment, and the environmental circuitry is configured to monitor the water of the environment to generate the first output.

18. The monitoring device of claim 17 wherein the environmental circuitry is configured to monitor a pressure of the water to generate the first output.

19. The monitoring device of claim 17 wherein the environmental circuitry is configured to monitor a temperature of the water to generate the first output.

20. The monitoring device of claim 17 wherein the environmental circuitry is configured to monitor a magnetic field in the water to generate the first output.

21. The monitoring device of claim 17 wherein the environmental circuitry is configured to monitor each of a pressure and a temperature of the water and a magnetic field in the water to generate the first output.

22. The monitoring device of claim 1 wherein the processing circuitry is configured to process one or more of the first, second and third outputs to remove at least some data of the one or more of the first, second and third outputs prior to the transmission of the signal.

23. The monitoring device of claim 1 wherein the aquatic organism is within water of the environment, and the transmitter is configured to transmit the signal into the water while the transmitter is submerged within the water.

24. The monitoring device of claim 1 wherein the transmitter is configured to transmit the signal comprising an acoustic signal.

25. An aquatic organism monitoring method comprising:
associating a monitoring device with an aquatic organism;
using the monitoring device, first sensing at least one environmental parameter regarding an environment of the associated aquatic organism;
using the monitoring device, second sensing at least one behavioral parameter of the associated aquatic organism;
using the monitoring device, third sensing at least one physiological parameter of the associated aquatic organism;
outputting information regarding one or more of the at least one environmental parameter, the at least one behavioral parameter, and the at least one physiological parameter externally of the monitoring device, wherein the outputting comprises transmitting an acoustic signal that includes the information externally of the monitoring device;
wherein the second sensing comprises sensing the at least one behavioral parameter indicative of movement of the aquatic organism; and
processing an output resulting from the second sensing to generate the information regarding the at least one behavioral parameter comprising a tail-beat frequency of the aquatic organism.

26. The method of claim 25 wherein the first sensing comprises sensing the at least one environmental parameter indicative of one or more of temperature, pressure, and magnetic field of the environment of the aquatic organism.

27. The method of claim 25 wherein the third sensing comprises sensing the at least one physiological parameter using electrocardiogram circuitry.

28. The method of claim 25 wherein the third sensing comprises sensing the at least one physiological parameter using electromyogram circuitry.

29. The method of claim 25 wherein the outputting comprises outputting the information regarding each of the at least one environmental parameter, the at least one behavioral parameter, and the at least one physiological parameter.

30. The method of claim 25 further comprising processing data regarding the environmental parameter and the at least one physiological parameter to generate the information prior to the outputting.

31. The method of claim 25 wherein the information regards the at least one environmental parameter, and wherein the information is devoid of information regarding location of the monitoring device and is devoid of information regarding location of the aquatic organism.

32. The method of claim 31 further comprising determining location of the monitoring device.

33. The method of claim 25 wherein the aquatic organism is within water of the environment, and the transmitting comprises transmitting the acoustic signal into the water while the monitoring device is submerged within the water.

34. The method of claim 25 wherein the transmitting comprises transmitting while the monitoring device is physically associated with the aquatic organism.

* * * * *

UNITED STATES PATENT AND TRADEMARK OFFICE
CERTIFICATE OF CORRECTION

Page 1 of 2

PATENT NO. : 12,099,048 B2
APPLICATION NO. : 16/951251
DATED : September 24, 2024
INVENTOR(S) : Z. Daniel Deng et al.

It is certified that error appears in the above-identified patent and that said Letters Patent is hereby corrected as shown below:

In the Drawings

Sheet 8 of 15, FIG. 9 – Replace lower left-most "124" with --62-- as shown on the attached drawing sheet In the Specification Column 5, Line 61 – Replace "a pressure sensor 54" with --a pressure sensor 52--

Column 11, Line 10 – Replace "a resonator 122" with --a resonator 62--

Column 12, Line 15 – Replace "external resonator 124" with --external resonator 62--

Signed and Sealed this
Twenty-sixth Day of August, 2025

Coke Morgan Stewart
*Acting Director of the United States Patent and Trademark Office*